United States Patent
Cox et al.

(10) Patent No.: US 10,045,790 B2
(45) Date of Patent: Aug. 14, 2018

(54) DEVICE AND METHOD FOR TREATING VASCULAR OCCLUSION

(71) Applicant: Inari Medical, Inc., Irvine, CA (US)

(72) Inventors: Brian J. Cox, Laguna Niguel, CA (US); Paul Lubock, Monarch Beach, CA (US); Robert F. Rosenbluth, Laguna Niguel, CA (US)

(73) Assignee: Inari Medical, Inc., Irvine, CA (US)

( * ) Notice: Subject to any disclaimer, the term of this patent is extended or adjusted under 35 U.S.C. 154(b) by 0 days.

(21) Appl. No.: 15/466,740

(22) Filed: Mar. 22, 2017

(65) Prior Publication Data
US 2017/0189041 A1    Jul. 6, 2017

Related U.S. Application Data

(63) Continuation of application No. 14/430,519, filed as application No. PCT/US2013/061470 on Sep. 24, 2013.

(Continued)

(51) Int. Cl.
*A61B 17/221*    (2006.01)
*A61B 17/22*     (2006.01)

(52) U.S. Cl.
CPC .. *A61B 17/221* (2013.01); *A61B 2017/22001* (2013.01); *A61B 2017/2212* (2013.01);
(Continued)

(58) Field of Classification Search
CPC .......... A61B 17/221; A61B 2017/2215; A61B 2017/22001; A61B 2017/22034;
(Continued)

(56) References Cited

U.S. PATENT DOCUMENTS 2,955,592 A    10/1960   Maclean et al.
3,435,826 A     4/1969   Fogarty
(Continued)

FOREIGN PATENT DOCUMENTS

EP     1867290 B1    12/2007
JP     6190049        7/1994
(Continued)

OTHER PUBLICATIONS

Gibbs, et al., "Temporary Stent as a bail-out device during percutaneous transluminal coronary angioplasty: preliminary clinical experience," British Heart Journal, 1994, 71:372-377, Oct. 12, 1993 6 pgs.
(Continued)

*Primary Examiner* — Eric Rosen
*Assistant Examiner* — Chima Igboko
(74) *Attorney, Agent, or Firm* — Perkins Coie LLP

(57) ABSTRACT

A system and method for managing an occlusion, such as a blood clot, within a lumen or passageway of a patient. More particularly, a system and method for rapidly restoring blood flow through an occlusion including a self-expanding, tubular member through which blood may flow when in an expanded state. The tubular member has a structure configured to engage the occlusive material, thereby allowing for extraction of at least a portion of the occlusive material. The system may further employ a material extraction member that is deployed distally of the tubular member.

25 Claims, 19 Drawing Sheets

Related U.S. Application Data

(60) Provisional application No. 61/705,129, filed on Sep. 24, 2012, provisional application No. 61/728,755, filed on Nov. 20, 2012, provisional application No. 61/750,277, filed on Jan. 8, 2013, provisional application No. 61/845,796, filed on Jul. 12, 2013, provisional application No. 61/864,356, filed on Aug. 9, 2013.

(52) U.S. Cl.
CPC ........... *A61B 2017/2215* (2013.01); *A61B 2017/22034* (2013.01); *A61B 2017/22061* (2013.01); *A61B 2017/22067* (2013.01)

(58) Field of Classification Search
CPC .......... A61B 17/22031; A61B 17/3207; A61B 17/320725; A61B 17/32075; A61B 2017/320716; A61B 2017/320733; A61B 2017/320741; A61B 17/22; A61B 17/22012; A61B 17/320708; A61B 17/320758; A61B 17/320783; A61B 2017/22081; A61B 17/22094; A61B 17/22035; A61B 17/22037; A61B 17/22051; A61B 17/22061; A61B 17/320766; A61B 17/320775; A61B 17/320791; A61F 2/01; A61F 2/013; A61F 2002/015; A61F 2002/011

See application file for complete search history.

(56) References Cited

U.S. PATENT DOCUMENTS

| | | |
|---|---|---|
| 3,923,065 A | 12/1975 | Nozick et al. |
| 4,030,503 A | 6/1977 | Clark, III |
| 4,650,466 A | 3/1987 | Luther |
| 4,873,978 A | 10/1989 | Ginsburg |
| 4,883,458 A | 11/1989 | Shiber |
| 4,890,611 A | 1/1990 | Monfort et al. |
| 5,011,488 A | 4/1991 | Ginsburg |
| 5,059,178 A | 10/1991 | Ya |
| 5,100,423 A | 3/1992 | Fearnot et al. |
| 5,102,415 A | 4/1992 | Guenther et al. |
| 5,129,910 A | 7/1992 | Phan et al. |
| 5,192,286 A | 3/1993 | Phan et al. |
| 5,192,290 A | 3/1993 | Hilal |
| 5,364,345 A | 11/1994 | Lowery et al. |
| 5,370,653 A | 12/1994 | Cragg |
| 5,443,443 A | 8/1995 | Shiber et al. |
| 5,476,450 A | 12/1995 | Ruggio |
| 5,490,859 A | 2/1996 | Mische et al. |
| 5,746,758 A | 5/1998 | Nordgren et al. |
| 5,749,858 A | 5/1998 | Cramer |
| 5,766,191 A | 6/1998 | Trerotola et al. |
| 5,827,304 A | 10/1998 | Hart |
| 5,868,708 A | 2/1999 | Hart et al. |
| 5,873,882 A | 2/1999 | Straub et al. |
| 5,876,414 A | 3/1999 | Straub et al. |
| 5,882,329 A | 3/1999 | Patterson et al. |
| 5,902,263 A | 5/1999 | Patterson et al. |
| 5,941,869 A | 8/1999 | Patterson et al. |
| 5,972,019 A | 10/1999 | Engelson et al. |
| 6,066,149 A | 5/2000 | Samson et al. |
| 6,066,158 A | 5/2000 | Engelson et al. |
| 6,152,946 A | 11/2000 | Broome et al. |
| 6,168,579 B1 | 1/2001 | Tsugita et al. |
| 6,203,561 B1 | 3/2001 | Ramee et al. |
| 6,221,006 B1 | 4/2001 | Dubrul et al. |
| 6,238,412 B1 | 5/2001 | Dubrul et al. |
| 6,254,571 B1 | 7/2001 | Hart |
| 6,258,115 B1 | 7/2001 | Dubrul et al. |
| 6,306,163 B1 | 10/2001 | Fitz |
| 6,364,895 B1 | 4/2002 | Greenhalgh et al. |
| 6,368,339 B1 | 4/2002 | Amplatz |
| 6,383,205 B1 | 5/2002 | Samson et al. |
| 6,413,235 B1 | 7/2002 | Parodi et al. |
| 6,423,032 B2 | 7/2002 | Parodi et al. |
| 6,440,148 B1 | 8/2002 | Shiber et al. |
| 6,454,741 B1 | 9/2002 | Muni et al. |
| 6,454,775 B1 | 9/2002 | Demarais et al. |
| 6,458,139 B1 | 10/2002 | Palmer et al. |
| 6,511,492 B1 | 1/2003 | Rosenbluth et al. |
| 6,514,273 B1 | 2/2003 | Voss et al. |
| 6,530,935 B2 | 3/2003 | Wensel et al. |
| 6,530,939 B1 | 3/2003 | Hopkins et al. |
| 6,544,279 B1 | 4/2003 | Hopkins et al. |
| 6,589,263 B1 | 7/2003 | Hopkins et al. |
| 6,596,011 B2 | 7/2003 | Johnson et al. |
| 6,602,271 B2 | 8/2003 | Adams et al. |
| 6,605,074 B2 | 8/2003 | Zadno-Azizi et al. |
| 6,605,102 B1 | 8/2003 | Mazzocchi et al. |
| 6,635,070 B2 | 10/2003 | Leeflang et al. |
| 6,645,222 B1 | 11/2003 | Parodi et al. |
| 6,660,013 B2 | 12/2003 | Rabiner et al. |
| 6,663,650 B2 | 12/2003 | Sepetka et al. |
| 6,685,722 B1 | 2/2004 | Rosenbluth et al. |
| 6,692,504 B2 | 2/2004 | Kurz et al. |
| 6,699,260 B2 | 3/2004 | Dubrul et al. |
| 6,755,722 B1 | 6/2004 | Horie et al. |
| 6,755,847 B2 | 6/2004 | Eskuri et al. |
| 6,767,353 B1 | 7/2004 | Shiber |
| 6,800,080 B1 | 10/2004 | Bates et al. |
| 6,939,361 B1 | 9/2005 | Kleshinski |
| 6,960,222 B2 | 11/2005 | Vo et al. |
| 7,004,954 B1 | 2/2006 | Voss et al. |
| 7,036,707 B2 | 5/2006 | Ezumi et al. |
| 7,052,500 B2 | 5/2006 | Bashiri et al. |
| 7,056,328 B2 | 6/2006 | Arnott et al. |
| 7,179,273 B1 | 2/2007 | Palmer et al. |
| 7,220,269 B1 | 5/2007 | Ansel et al. |
| 7,232,432 B2 | 6/2007 | Fulton et al. |
| 7,244,243 B2 | 7/2007 | Lary |
| 7,285,126 B2 | 10/2007 | Sepetka et al. |
| 7,306,618 B2 | 12/2007 | Demond et al. |
| 7,320,698 B2 | 1/2008 | Eskuri |
| 7,323,002 B2 | 1/2008 | Johnson et al. |
| 7,331,980 B2 | 2/2008 | Dubrul et al. |
| 7,578,830 B2 | 8/2009 | Kusleika et al. |
| 7,621,870 B2 | 11/2009 | Berrada et al. |
| 7,691,121 B2 | 4/2010 | Rosenbluth et al. |
| 7,763,010 B2 | 7/2010 | Strang et al. |
| 7,766,934 B2 | 8/2010 | Pal et al. |
| 7,905,896 B2 | 3/2011 | Straub et al. |
| 7,938,820 B2 | 5/2011 | Webster et al. |
| 7,993,302 B2 | 8/2011 | Hebert et al. |
| 7,993,363 B2 | 8/2011 | Demond et al. |
| 8,006,757 B2 | 8/2011 | Hackworth et al. |
| 8,043,313 B2 | 10/2011 | Krolik et al. |
| 8,052,640 B2 | 11/2011 | Fiorella et al. |
| 8,066,757 B2 | 11/2011 | Ferrera et al. |
| 8,070,791 B2 | 12/2011 | Ferrera et al. |
| 8,075,510 B2 | 12/2011 | Aklog et al. |
| 8,088,140 B2 | 1/2012 | Ferrera et al. |
| 8,100,935 B2 | 1/2012 | Rosenbluth et al. |
| 8,109,962 B2 | 2/2012 | Pal et al. |
| 8,118,829 B2 | 2/2012 | Carrison et al. |
| 8,197,493 B2 | 6/2012 | Ferrera et al. |
| 8,246,641 B2 | 8/2012 | Osborne et al. |
| 8,261,648 B1 | 9/2012 | Marchand et al. |
| 8,298,257 B2 | 10/2012 | Sepetka et al. |
| 8,317,748 B2 | 11/2012 | Fiorella et al. |
| RE43,902 E | 1/2013 | Hopkins et al. |
| 8,357,178 B2 | 1/2013 | Grandfield et al. |
| 8,361,104 B2 | 1/2013 | Jones et al. |
| 8,409,215 B2 | 4/2013 | Sepetka et al. |
| 8,486,105 B2 | 7/2013 | Demond et al. |
| 8,512,352 B2 | 8/2013 | Martin et al. |
| 8,535,334 B2 | 9/2013 | Martin et al. |
| 8,545,526 B2 | 10/2013 | Martin et al. |
| 8,568,432 B2 | 10/2013 | Straub et al. |
| 8,574,262 B2 | 11/2013 | Ferrera et al. |
| 8,579,915 B2 | 11/2013 | French et al. |

(56) References Cited

U.S. PATENT DOCUMENTS

| | | |
|---|---|---|
| 8,585,713 B2 | 11/2013 | Ferrera et al. |
| 8,696,622 B2 | 4/2014 | Fiorella et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,345 B2 | 8/2014 | Martin et al. |
| 8,801,748 B2 | 8/2014 | Martin et al. |
| 8,820,207 B2 | 9/2014 | Marchand et al. |
| 8,826,791 B2 | 9/2014 | Thompson et al. |
| 8,828,044 B2 | 9/2014 | Aggerholm et al. |
| 8,833,224 B2 | 9/2014 | Thompson et al. |
| 8,852,205 B2 | 10/2014 | Brady et al. |
| 8,852,226 B2 | 10/2014 | Gilson et al. |
| 8,932,319 B2 | 1/2015 | Martin et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 8,992,504 B2 | 3/2015 | Castella et al. |
| 9,149,609 B2 | 10/2015 | Ansel et al. |
| 9,161,766 B2 | 10/2015 | Slee et al. |
| 9,204,887 B2 | 12/2015 | Cully et al. |
| 9,259,237 B2 | 2/2016 | Quick et al. |
| 9,283,066 B2 | 3/2016 | Hopkins et al. |
| 9,439,664 B2 | 9/2016 | Sos |
| 9,456,834 B2 | 10/2016 | Folk et al. |
| 9,463,036 B2 | 10/2016 | Brady et al. |
| 9,757,137 B2 | 9/2017 | Krolik et al. |
| 2001/0041909 A1 | 11/2001 | Tsugita et al. |
| 2002/0022858 A1 | 2/2002 | Demond et al. |
| 2002/0026211 A1 | 2/2002 | Khosravi et al. |
| 2002/0120277 A1 | 8/2002 | Hauschild et al. |
| 2002/0147458 A1 | 10/2002 | Hiblar et al. |
| 2002/0156457 A1 | 10/2002 | Fisher |
| 2003/0100919 A1 | 5/2003 | Hopkins et al. |
| 2003/0114875 A1 | 6/2003 | Sjostrom et al. |
| 2003/0125663 A1 | 7/2003 | Coleman et al. |
| 2003/0135230 A1 | 7/2003 | Massey et al. |
| 2003/0191516 A1 | 10/2003 | Weldon et al. |
| 2004/0068288 A1 | 4/2004 | Palmer et al. |
| 2004/0073243 A1 | 4/2004 | Sepetka et al. |
| 2004/0133232 A1 | 7/2004 | Rosenbluth et al. |
| 2004/0167567 A1 | 8/2004 | Cano et al. |
| 2004/0199201 A1 | 10/2004 | Kellett et al. |
| 2005/0055047 A1 | 3/2005 | Greenhalgh |
| 2005/0119668 A1 | 6/2005 | Teague et al. |
| 2005/0283186 A1* | 12/2005 | Berrada ............... A61F 2/013 606/200 |
| 2006/0020286 A1 | 1/2006 | Niermann |
| 2006/0047286 A1 | 3/2006 | West et al. |
| 2006/0100662 A1 | 5/2006 | Daniel et al. |
| 2006/0224177 A1 | 10/2006 | Finitsis |
| 2006/0229645 A1 | 10/2006 | Bonnette et al. |
| 2006/0253145 A1 | 11/2006 | Lucas |
| 2006/0282111 A1 | 12/2006 | Morsi |
| 2007/0118165 A1 | 5/2007 | DeMello et al. |
| 2007/0161963 A1 | 7/2007 | Smalling |
| 2007/0179513 A1 | 8/2007 | Deutsch |
| 2007/0191866 A1 | 8/2007 | Palmer et al. |
| 2007/0198028 A1 | 8/2007 | Miloslavski et al. |
| 2007/0208361 A1 | 9/2007 | Okushi et al. |
| 2007/0208367 A1 | 9/2007 | Fiorella et al. |
| 2007/0213753 A1 | 9/2007 | Waller |
| 2007/0255252 A1 | 11/2007 | Mehta |
| 2007/0288054 A1 | 12/2007 | Tanaka et al. |
| 2008/0015541 A1 | 1/2008 | Rosenbluth et al. |
| 2008/0167678 A1 | 7/2008 | Morsi |
| 2008/0228209 A1 | 9/2008 | DeMello et al. |
| 2008/0269798 A1 | 10/2008 | Ramzipoor et al. |
| 2009/0054918 A1 | 2/2009 | Henson |
| 2009/0062841 A1 | 3/2009 | Amplatz et al. |
| 2009/0069828 A1 | 3/2009 | Martin et al. |
| 2009/0163846 A1 | 6/2009 | Aklog et al. |
| 2009/0182362 A1 | 7/2009 | Thompson et al. |
| 2009/0292307 A1 | 11/2009 | Razack |
| 2009/0299393 A1* | 12/2009 | Martin ............... A61B 17/221 606/159 |
| 2010/0114113 A1 | 5/2010 | Dubrul et al. |
| 2010/0204712 A1 | 8/2010 | Mallaby |
| 2010/0249815 A1 | 9/2010 | Jantzen et al. |
| 2010/0268264 A1 | 10/2010 | Bonnette et al. |
| 2010/0318178 A1 | 12/2010 | Rapaport et al. |
| 2011/0060212 A1 | 3/2011 | Slee et al. |
| 2011/0152993 A1 | 6/2011 | Marchand et al. |
| 2011/0190806 A1 | 8/2011 | Wittens |
| 2011/0196414 A1 | 8/2011 | Porter et al. |
| 2011/0213290 A1 | 9/2011 | Chin et al. |
| 2011/0213403 A1 | 9/2011 | Aboytes |
| 2011/0224707 A1 | 9/2011 | Miloslavski et al. |
| 2011/0251629 A1 | 10/2011 | Galdonik et al. |
| 2011/0264133 A1 | 10/2011 | Hanlon et al. |
| 2012/0059309 A1 | 3/2012 | di Palma et al. |
| 2012/0089216 A1 | 4/2012 | Rapaport et al. |
| 2012/0101510 A1 | 4/2012 | Lenker et al. |
| 2012/0143239 A1 | 6/2012 | Aklog et al. |
| 2012/0165919 A1 | 6/2012 | Cox et al. |
| 2012/0179181 A1 | 7/2012 | Straub et al. |
| 2012/0197277 A1* | 8/2012 | Stinis ............... A61B 17/221 606/159 |
| 2012/0232655 A1 | 9/2012 | Lorrison et al. |
| 2012/0271231 A1 | 10/2012 | Agrawal |
| 2012/0277788 A1 | 11/2012 | Cattaneo et al. |
| 2013/0066348 A1 | 3/2013 | Fiorella et al. |
| 2013/0144326 A1 | 6/2013 | Brady et al. |
| 2013/0165871 A1 | 6/2013 | Fiorella et al. |
| 2013/0197567 A1 | 8/2013 | Brady et al. |
| 2013/0317589 A1 | 11/2013 | Martin et al. |
| 2013/0345739 A1 | 12/2013 | Brady et al. |
| 2014/0005712 A1 | 1/2014 | Martin et al. |
| 2014/0005713 A1 | 1/2014 | Bowman |
| 2014/0005715 A1 | 1/2014 | Castella et al. |
| 2014/0005717 A1 | 1/2014 | Martin et al. |
| 2014/0031856 A1 | 1/2014 | Martin et al. |
| 2014/0046243 A1 | 2/2014 | Ray et al. |
| 2014/0121672 A1 | 5/2014 | Folk et al. |
| 2014/0180397 A1 | 6/2014 | Gerberding et al. |
| 2014/0188143 A1 | 7/2014 | Martin et al. |
| 2014/0236219 A1 | 8/2014 | Dubrul et al. |
| 2014/0243882 A1 | 8/2014 | Ma et al. |
| 2014/0318354 A1 | 10/2014 | Thompson et al. |
| 2015/0018860 A1 | 1/2015 | Quick et al. |
| 2015/0018929 A1 | 1/2015 | Martin et al. |
| 2015/0127035 A1 | 5/2015 | Trapp et al. |
| 2015/0150672 A1 | 6/2015 | Ma et al. |
| 2015/0190156 A1 | 7/2015 | Ulm et al. |
| 2015/0196380 A1 | 7/2015 | Berrada et al. |
| 2015/0196744 A1 | 7/2015 | Aboytes et al. |
| 2015/0209058 A1 | 7/2015 | Ferrera et al. |
| 2015/0209165 A1 | 7/2015 | Grandfield et al. |
| 2015/0238207 A1 | 8/2015 | Cox et al. |
| 2015/0250578 A1 | 9/2015 | Cook et al. |
| 2015/0265299 A1 | 9/2015 | Cooper et al. |
| 2015/0305756 A1 | 10/2015 | Rosenbluth et al. |
| 2015/0352325 A1 | 12/2015 | Quick |
| 2015/0360001 A1 | 12/2015 | Quick |
| 2015/0374391 A1 | 12/2015 | Quick et al. |
| 2016/0008014 A1 | 1/2016 | Rosenbluth et al. |
| 2016/0030155 A1 | 2/2016 | Cox et al. |
| 2016/0143721 A1 | 5/2016 | Rosenbluth et al. |
| 2016/0367285 A1 | 12/2016 | Sos |
| 2017/0112513 A1 | 4/2017 | Marchand et al. |

FOREIGN PATENT DOCUMENTS

| | | |
|---|---|---|
| JP | 2004097807 | 4/2004 |
| JP | 2005-095242 | 4/2005 |
| JP | 2005230132 | 9/2005 |
| JP | 2005323702 | 11/2005 |
| JP | 2006094876 | 4/2006 |
| WO | WO-1997017889 | 5/1997 |
| WO | WO 98/38920 A1 | 9/1998 |
| WO | WO-1999044542 | 9/1999 |
| WO | WO-2012011097 A1 | 9/1999 |
| WO | WO 2000/053120 A1 | 9/2000 |

(56) References Cited

FOREIGN PATENT DOCUMENTS

| WO | WO 03/015840 A2 | 2/2003 |
| WO | WO 2004/093696 A1 | 11/2004 |
| WO | WO-2005046736 | 5/2005 |
| WO | WO-2006110186 | 10/2006 |
| WO | WO-2007092820 | 8/2007 |
| WO | WO-2009155571 | 12/2009 |
| WO | WO-2010010545 | 1/2010 |
| WO | WO-2010023671 | 3/2010 |
| WO | WO-2010049121 | 5/2010 |
| WO | WO-2010102307 | 9/2010 |
| WO | WO-2011054531 | 5/2011 |
| WO | WO-2012009675 | 1/2012 |
| WO | WO-2012065748 | 5/2012 |
| WO | WO-2014047650 | 3/2014 |
| WO | WO-2014081892 | 5/2014 |
| WO | WO 2015/006782 A1 | 1/2015 |
| WO | WO 2015/061365 A1 | 4/2015 |

OTHER PUBLICATIONS

Goldhaber, S. et al. "Percutaneous Mechanical Thrombectomy for Acute Pulmonary Embolism—A Double-Edged Sword", American College of CHEST Physicians, Aug. 2007: 132:2, 363-372.

Goldhaber, S., "Advanced treatment strategies for acute pulmonary embolism, including thrombolysis and embolectomy", Journal of Thrombosis and Haemostasis, 2009: 7 (Suppl. 1): 322-327.

Gupta, S. et al., "Acute Pulmonary Embolism Advances in Treatment", JAPI, Association of Physicians India, Mar. 2008, vol. 56, 185-191.

Konstantinides, S. et al., "Pulmonary embolism: risk assessment and management", European Society of Cardiology European Heart Journal, Sep. 7, 2012:33, 3014-3022.

Konstantinides, S. et al., "Pulmonary embolism hotline 2012—Recent and expected trials", Thrombosis and Haemostasis, Jan. 9, 2013:33 43-50.

Kucher, N. et al., "Percutaneous Catheter Thrombectomy Device for Acute Pulmonary Embolism: In Vitro and in Vivo Testing", Circulation, Sep. 2005:112:e28-e32.

Kucher, N. et al., "Management of Massive Pulmonary Embolism", Radiology, Sep. 2005:236:3 852-858.

Kucher, N., "Catheter Interventions in Massive Pulmonary Embolism", Cardiology Rounds, Mar. 2006 vol. 10, Issue 3, 6 pages.

Kuo, W. et al., "Catheter-directed Therapy for the Treatment of Massive Pulmonary Embolism: Systematic Review and Meta-analysis of Modern Techniques", Journal of Vascular and Interventional Radiology, Nov. 2009:20:1431-1440.

Kuo, W. et al., "Catheter-Directed Embolectomy, Fragmentation, and Thrombolysis for the Treatment of Massive Pulmonary Embolism After Failure of Systemic Thrombolysis", American College of CHEST Physicians 2008: 134:250-254.

Kuo, W. MD, "Endovascular Therapy for Acute Pulmonary Embolism", Continuing Medical Education Society of Interventional Radiology ("CME") Journal of Vascular and Interventional Radiology, Feb. 2012: 23:167-179.

Lee, L. et al, "Massive pulmonary embolism: review of management strategies with a focus on catheter-based techniques", Expert Rev. Cardiovasc. Ther. 8(6), 863-873 (2010).

Liu, S. et al, "Massive Pulmonary Embolism: Treatment with the Rotarex Thrombectomy System", Cardiovascular Interventional Radiology, 2011: 34:106-113.

Muller-Hulsbeck, S. et al. "Mechanical Thrombectomy of Major and Massive Pulmonary Embolism with Use of the Amplatz Thrombectomy Device", Investigative Radiology Jun. 2001:36:6:317-322.

Reekers, J. et al., "Mechanical Thrombectomy for Early Treatment of Massive Pulmonary Embolism", CardioVascular and Interventional Radiology, 2003: 26:246-250.

Schmitz-Rode et al., "New Mesh Basket for Percutaneous Removal of Wall-Adherent Thrombi in Dialysis Shunts," Cardiovasc Intervent Radio116:7-10 1993 4 pgs.

Schmitz-Rode et al., "Temporary Pulmonary Stent Placement as Emergency Treatment of Pulmonary Embolism," Journal of the American College of Cardiology, vol. 48, No. 4, 2006 (5 pgs.).

Schmitz-Rode, T. et al., "Massive Pulmonary Embolism: Percutaneous Emergency Treatment by Pictail Rotation Catheter", JACC Journal of the American College of Cardiology, Aug. 2000:36:2:375-380.

Tapson, V., "Acute Pulmonary Embolism", The New England Journal of Medicine, Mar. 6, 2008:358:2037-52.

Truong et al., "Mechanical Thrombectomy of Iliocaval Thrombosis Using a Protective Expandable Sheath," Cardiovasc Intervent Radiol 27-254-258, 2004, 5 pgs.

Turk et al., "ADAPT FAST study: a direct aspiration first pass technique for acute stroke thrombectomy." J Neuro Intervent Surg, vol. 6, 2014, 6 pages.

Uflacker, R., "Interventional Therapy for Pulmonary Embolism", Journal of Vascular and Interventional Radiology Feb. 2001: 12:147-164.

Verma, R., MD et al. "Evaluation of a Newly Developed Percutaneous Thrombectomy Basket Device in Sheep With Central Pulmonary Embolisms", *Investigative Radiology*, Oct. 2006, 41, 729-734.

Kucher, N. et al., "Randomized, Controlled Trial of Ultrasound-Assisted Catheter-Directed Thrombolysis for Acute Intermediate-Risk Pulmonary Embolism." Circulation, 2014, 129, pp. 9 pages.

Spiotta, A et al., "Evolution of thrombectomy approaches and devices for acute stroke: a technical review." J NeuroIntervent Surg 2015, 7, pp. 7 pages.

Svilaas, T. et al., "Thrombus Aspiration During Primary Percutaneous Coronary Intervention." The New England Journal of Medicine, 2008, vol. 358, No. 6, 11 pages.

The Penumbra Pivotal Stroke Trial Investigators, "The Penumbra Pivotal Stroke Trial: Safety and Effectiveness of a New Generation of Mechanical Devices for Clot Removal in Intracranial Large Vessel Occlusive Disease." Stroke, 2009, 40: p. 9 pages.

\* cited by examiner

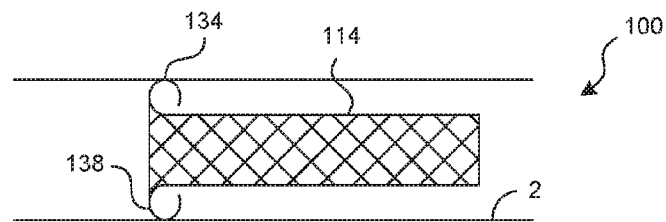
FIG. 27
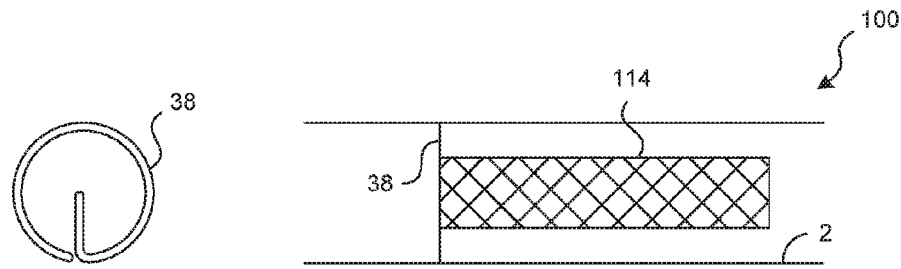
FIG. 28A  FIG. 28B
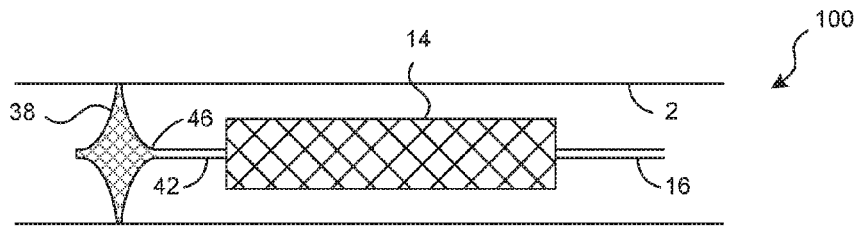
FIG. 29

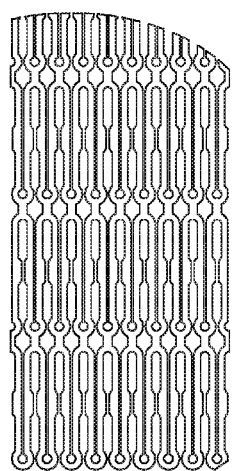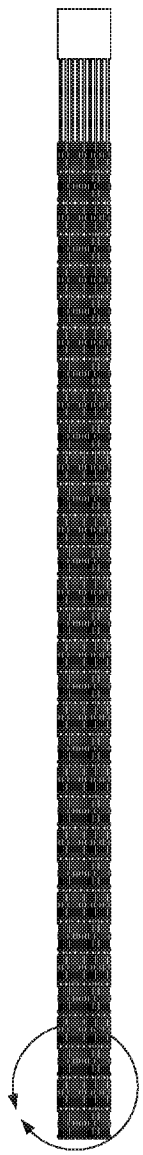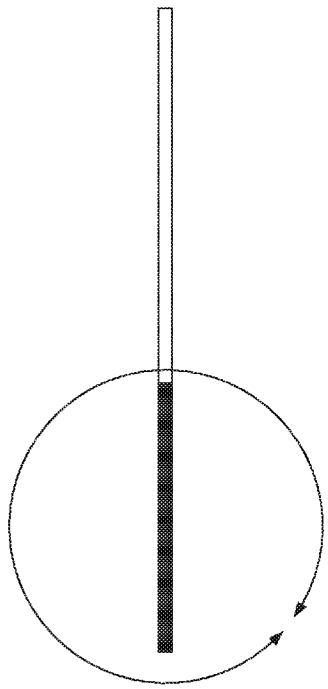
FIG. 40A
FIG. 40B
FIG. 40C

DEVICE AND METHOD FOR TREATING VASCULAR OCCLUSION

CROSS-REFERENCE TO RELATED APPLICATIONS

This application is a continuation of U.S. Non-Provisional application Ser. No. 14/430,519 filed on Mar. 23, 2015 entitled Device and Method for Treating Vascular Occlusion, which is a 35 U.S.C. 371 of International Patent Application No. PCT/US2013/061470 filed on Sep. 24, 2013 entitled Device and Method for Treating Vascular Occlusion, which Application claims priority to U.S. Provisional Application Ser. No. 61/864,356 filed Aug. 9, 2013 entitled Devices and Methods for Treatment of Vascular Occlusion; U.S. Provisional Application Ser. No. 61/845,796 filed Jul. 12, 2013 entitled Devices and Methods for Treatment of Vascular Occlusion; U.S. Provisional Application Ser. No. 61/750,277 filed Jan. 8, 2013 entitled Devices and Methods for Treatment of Vascular Occlusion; U.S. Provisional Application Ser. No. 61/728,775 filed Nov. 20, 2012 entitled Devices and Methods for Treatment of Vascular Occlusion; and U.S. Provisional Application Ser. No. 61/705,129 filed Sep. 24, 2012 entitled Devices and Methods for Treatment of Vascular Occlusion; each of which are incorporated herein by reference in their entireties.

TECHNICAL FIELD

This invention relates to a system and method for endovascular treatment of blood clots obstructing passageways in the circulatory system.

BACKGROUND

Thromboembolism is the formation in a blood vessel of a clot (thrombus) that breaks loose (embolizes) and is carried by the blood stream to another location in the circulatory system resulting in a clot or obstruction at that new location. For example, a clot may embolize and plug a vessel in the lungs (pulmonary embolism), the brain (stroke), the gastrointestinal tract, the kidneys, or the legs. Thromboembolism is a significant cause of morbidity (disease) and mortality (death), especially in adults. A thromboembolism can be sudden and massive or it may be small and multiple. A thromboembolism can be any size and a thromboembolic event can happen at any time.

When a thrombus forms in the venous circulation of the body it often embolizes to the lungs. Such a thrombus typically embolizes from the veins of the legs, pelvis, or inferior vena cava and travels to the right heart cavities and then into the pulmonary arteries thus resulting in a pulmonary embolism.

A pulmonary embolism results in right heart failure and decreased blood flow through the lungs with subsequent decreased oxygenation of the lungs, heart and the rest of the body. More specifically, when such a thrombus enters the pulmonary arteries, obstruction and spasm of the different arteries of the lung occurs which further decreases blood flow and gaseous exchange through the lung tissue resulting in pulmonary edema. All of these factors decrease the oxygen in the blood in the left heart. As a result, the oxygenated blood supplied by the coronary arteries to the musculature of both the left and right heart is insufficient for proper contractions of the muscle which further decreases the entire oxygenated blood flow to the rest of the body. This often leads to heart dysfunction and specifically right ventricle dysfunction.

This condition is relatively common and has many causes. Some of the more common causes are prolonged inactivity such as bed rest, extended sitting (e.g., lengthy aircraft travel), dehydration, extensive surgery or protracted disease. Almost all of these causes are characterized by the blood of the inferior peripheral major circulatory system coagulating to varying degrees and resulting in permanent drainage problems.

There exist a number of approaches to treating thromboembolism and particularly pulmonary embolism. Some of those approaches include the use of anticoagulants, thrombolytics and endovascular attempts at removal of the emboli from the pulmonary artery. The endovascular attempts often rely on catheterization of the affected vessels and application of chemical or mechanical agents or both to disintegrate the clot. Invasive surgical intervention in which the emboli is removed by accessing the chest cavity, opening the embolized pulmonary artery and/or its branches and removing the clot is also possible.

The prior approaches to treatment, however, are lacking. For example, the use of agents such as anticoagulants and/or thrombolytics to reduce or remove a pulmonary embolism typically takes a prolonged period of time, e.g., hours and even days, before the treatment is effective. Moreover, such agents can cause hemorrhage in a patient.

And the known mechanical devices for removing an embolism are typically highly complex and prone to cause undue trauma to the vessel. Moreover, such known devices are difficult and expensive to manufacture.

Lastly, the known treatment methods do not emphasize sufficiently the goal of urgently restoring blood flow through the thrombus once the thrombus has been identified. In other words, the known methods focus primarily and firstly on overall clot reduction and removal instead of first focusing on relief of the acute blockage condition followed then by the goal of clot reduction and removal. Hence, known methods are not providing optimal patient care, particularly as such care relates to treatment of a pulmonary embolism.

SUMMARY

The above described shortcomings of the existing systems and approaches for treating an occlusion in a lumen of a patient, such as a thromboembolism and particularly a pulmonary embolism, are improved upon by the systems and methods of the present invention. These improvements are achieved in certain embodiments of the present invention, in part, by providing an occlusion management system comprising a catheter, a pusher, and a tubular member reversibly restrained in a compressed state within a lumen of the catheter and radially expanded from the compressed state upon retraction of the catheter relative to the pusher.

These improvements are further achieved in certain embodiments of the present invention, in part, by providing occlusion management system comprising a catheter, a pusher, a tubular member attached to a distal end of the pusher, and an extraction member extending distally of a distal end of the cylindrical member having a diameter larger than a diameter of the cylindrical member.

These improvements are further achieved in certain embodiments of the present invention, in part, by a method for management of an occlusion in a lumen comprising the steps of: creating a passage for fluid flow through occlusive material in a lumen of a patient, engaging a portion of the occlusive material with at least a portion of a tubular member; and extracting a portion of the occlusive material from the lumen of the patient.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 27 is a partial cutaway view of a portion of an occlusion management system within a lumen of a patient according to one embodiment of the present invention.

FIG. 28A is an elevation view of a portion of an occlusion management system according to one embodiment of the present invention.

FIG. 28B is a partial cutaway view of a portion of an occlusion management system within lumen of a patient according to one embodiment of the present invention.

FIG. 29 is a partial cutaway view of a portion of an occlusion management system within a lumen of a patient according to one embodiment of the present invention.

FIG. 40A-40C are elevation views of portions of an occlusion management system according to one embodiment of the present invention.

DETAILED DESCRIPTION

Figure 1:
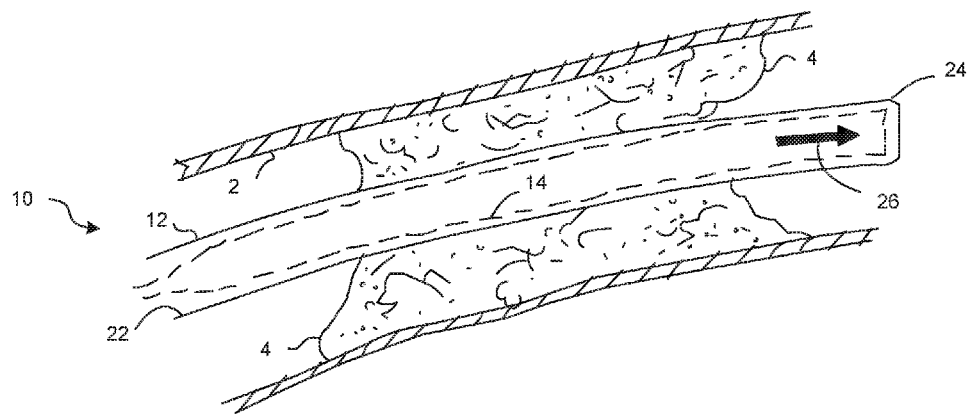
FIG. 1 is a partial cutaway view of a portion of an occlusion management system within a lumen of a patient according to one embodiment of the present invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Methods and systems according to the present invention are broadly directed to treating a blood vessel or other body lumen. More particularly, the present invention is directed to systems and methods for disrupting, dissolving, and/or otherwise removing occlusive materials, such as thrombus, from a treatment site, such as a blood vessel.

With reference to FIGS. 1-6, in one embodiment of the present invention, an occlusion management system 10 employs a catheter 12 and a flow restoration member 14. The flow restoration member 14 is radially expandable from a compressed delivery state, to a radially expanded, minimum energy state having at least, in part, a hollow cylindrical or tubular shape. A distal end 18 of a pusher 16 is attached to a proximal portion 20 of the flow restoration member 14.

The flow restoration member 14 may be formed of a porous mesh or scaffold. The mesh or scaffold may be formed at least in part by a braid of filaments or fabricated by methods known in the art of stent manufacturing including but not limited to conventional machining, laser cutting, electrical discharge machining (EDM) and photochemical etching.

In operation, the pusher 16 and the attached compressed flow restoration member 14 are inserted into a lumen 22 of the catheter 12. The catheter 12 is advanced through a lumen 2 of a patient, e.g. a blood vessel 2, to a site within the lumen 2 at which occlusive material 4, such as a thrombus or an embolus, is located. The catheter 12 is advanced in the direction of arrow 26 through the occlusive material 4 until a distal end 24 of the catheter 12 passes entirely through the occlusive material 4, as shown in FIG. 1.

Figure 2:
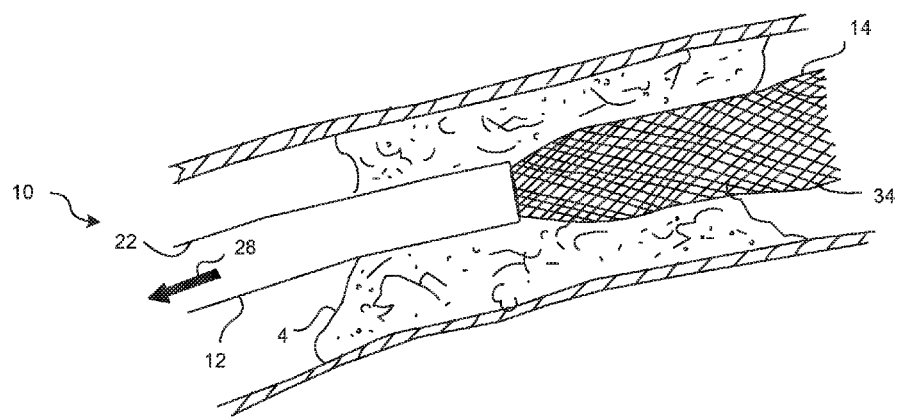
FIG. 2 is a partial cutaway view of a portion of an occlusion management system within a lumen of a patient according to one embodiment of the present invention.

With reference to FIG. 2, the catheter 12 is then retracted relative to the pusher 16 and flow restoration member 14 in the direction of arrow 28. As the flow restoration member 14 is exposed from the retracting distal end of the catheter 12, the flow restoration member 14 radially expands within the occlusive material 4 to an intermediate diameter larger than a diameter of the member 14 in the compressed delivery state and smaller than a diameter of the member 14 in the expanded, minimum energy state. The structure and outer surface of the flow restoration member 14 is configured such that the mesh or scaffold of the flow restoration member 14 engages the occlusive material 4 when it is exposed from the constraint of the catheter 12. As shown in FIG. 2, the catheter 12 is retracted in the direction of arrow 28 to an extent that allows for the radial expansion of an entire length of the flow restoration member 14.

Figure 3:
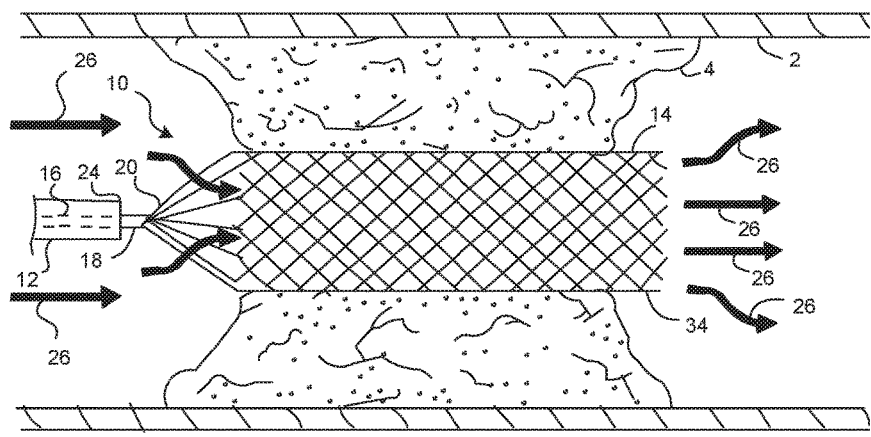
FIG. 3 is a partial cutaway view of a portion of an occlusion management system within a lumen of a patient according to one embodiment of the present invention.

As shown in FIG. 3, when catheter 12 is retracted sufficiently to allow expansion of the entire length of the flow restoration member 14, fluid or blood may enter the open, proximal portion 20 of the flow restoration member 14 in the direction of arrows 30, flow through the hollow interior of the flow restoration member 14, and exit through a open, distal portion 34 of the flow restoration member 14. Thereby, allowing for a rapid restoration of blood flow through the lumen 2.

Figure 4:
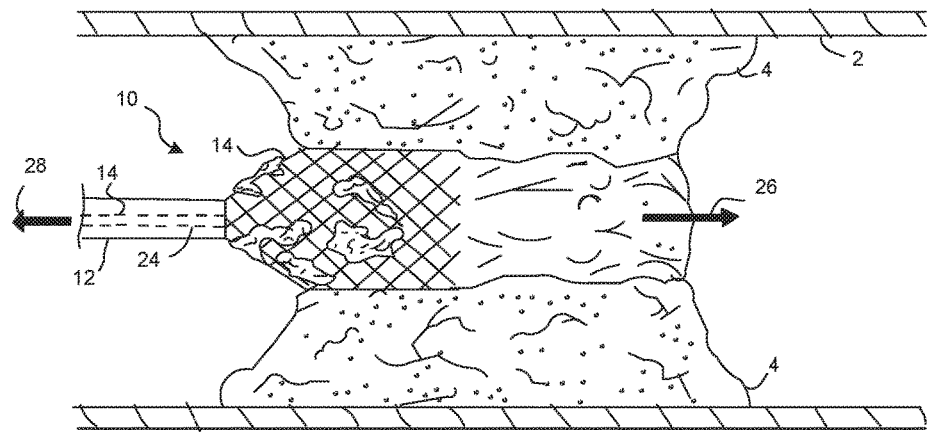
FIG. 4 is a partial cutaway view of a portion of an occlusion management system within a lumen of a patient according to one embodiment of the present invention.

As shown in FIG. 4, the pusher 16 is then retracted relative to the catheter in the direction of the arrow 28, thereby pulling the length of the flow restoration member 14 through the occlusive material 4. The pusher 16 is retracted such that the flow restoration member 14 is pulled towards the distal end 24 of the catheter 12 and back into the lumen 22 of the catheter 12. As the flow restoration member 14 is pulled through the occlusive material 4, the occlusive material 4 engaged with the flow restoration member 14 is also pulled along and removed.

Hence, while restoring flow through the lumen 2, the flow restoration member 14 may also function to remove or extract at least a portion of the occlusive material 4 from the lumen 2. Finally, the flow restoration member 14 and the engaged occlusive material 4 is pulled back into the lumen 22 of the catheter 12 and the system 10 is withdrawn from the patient.

Figure 5:
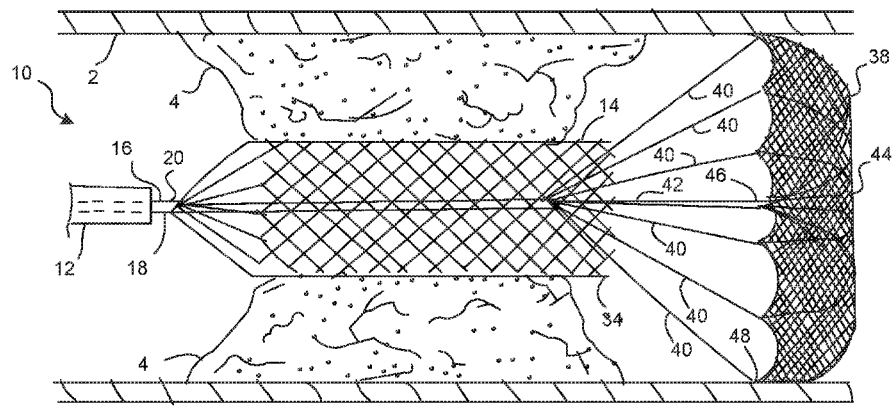
FIG. 5 is a partial cutaway view of a portion of an occlusion management system within a lumen of a patient according to one embodiment of the present invention.
Figure 6:
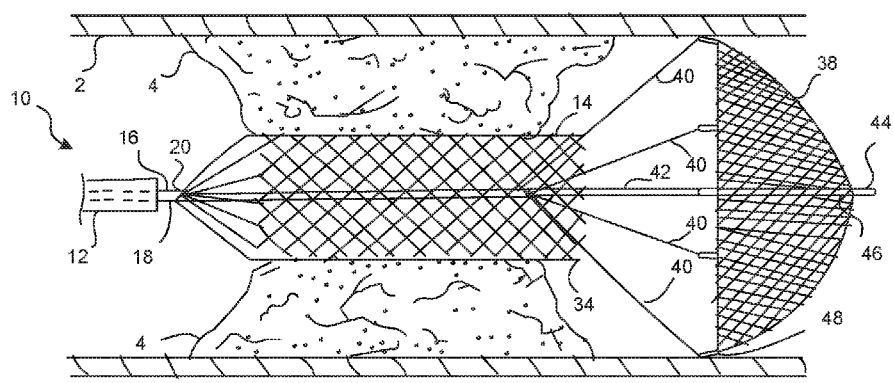
FIG. 6 is a partial cutaway view of a portion of an occlusion management system within a lumen of a patient according to one embodiment of the present invention.
Figure 7:
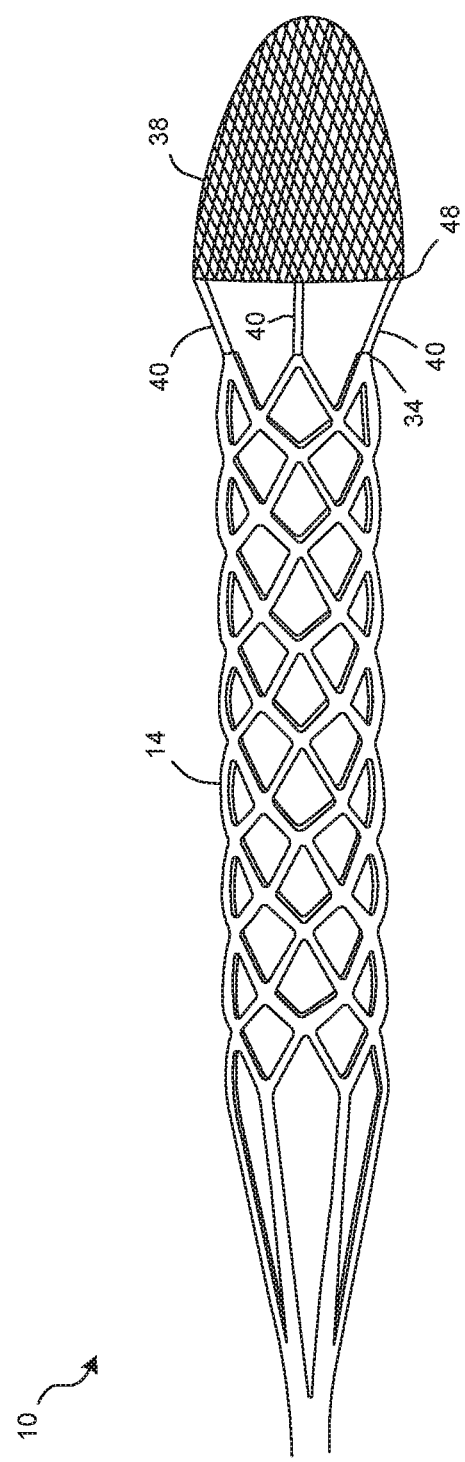
FIG. 7 is a side elevation view of a portion of an occlusion management system according to one embodiment of the present invention.
Figure 8:
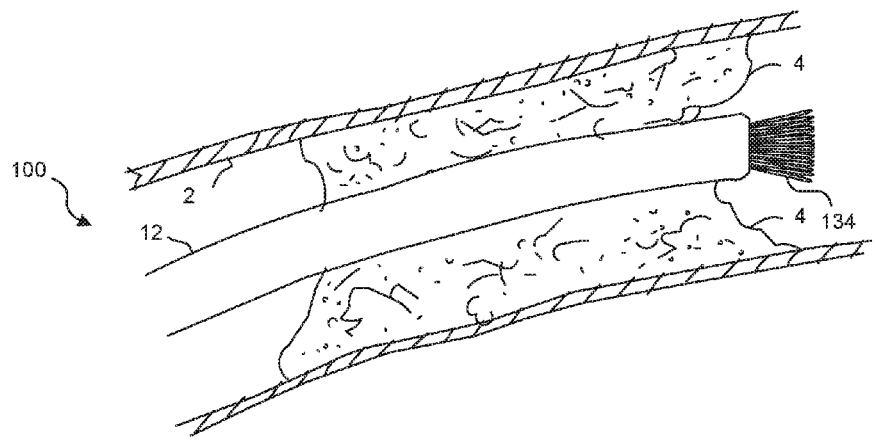
FIG. 8 is a partial cutaway view of a portion of an occlusion management system within a lumen of a patient according to one embodiment of the present invention.
Figure 9:
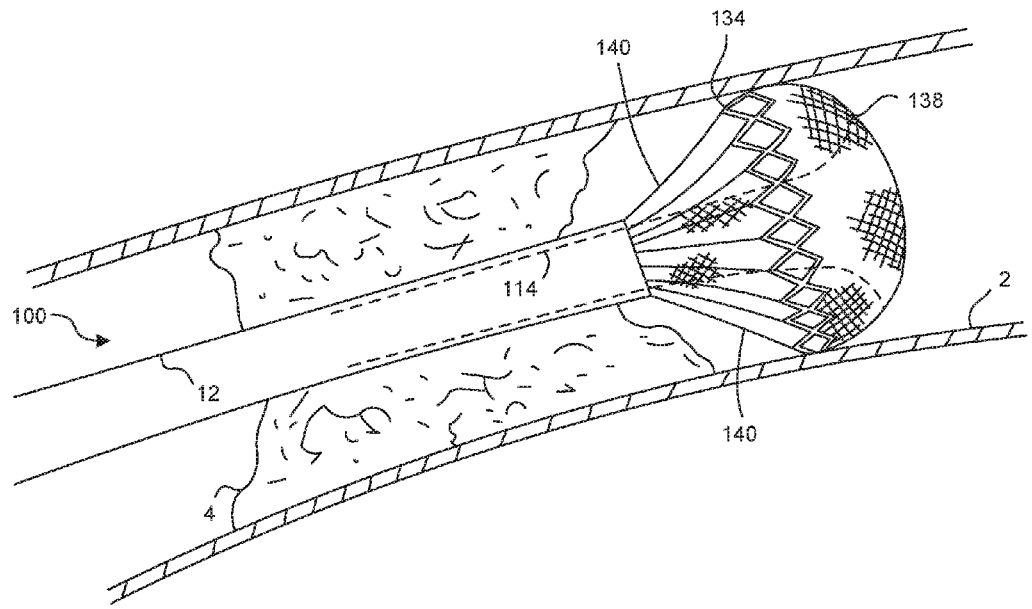
FIG. 9 is a partial cutaway view of a portion of an occlusion management system within a lumen of a patient according to one embodiment of the present invention.

In one embodiment of the present invention, as shown in FIGS. 5-7, the occlusion management system 10 may further employ an extraction member 38 for extraction or removal of the occlusive material 4, such as an embolus. The extraction member 38 may have an umbrella-like configuration, as shown in FIG. 5; a conical configuration, as shown in FIG. 6; or a cup-like configuration, as shown in FIG. 7. The extraction member 38 expands from a compressed diameter to an expanded diameter that is greater than a diameter of the expanded flow restoration member 14 and approximately equal to a diameter of the lumen 2.

The extraction member 38 may be attached directly to the flow restoration member 14 or to a separate structure that is deployed through the flow restoration member 14 either before or after deployment of the flow restoration member 14. For example, as shown in FIGS. 5 and 6, a distal portion 44 of the extraction member 38 may be attached to a distal end 46 of a delivery element 42. The delivery element 42 may be formed of a separate, transposable element that is located within a lumen of the pusher 16. One or more tethers 40 may statically attach a proximal periphery 48 of the extraction member 38 to the delivery element 42 proximally of the distal end 46 of the delivery element 42. The tethers 40 facilitate compression and retraction of the extraction member 38 back into the catheter 12. Alternatively, the tethers 40 may be transposable independent of the delivery element 42. For example, the tethers 40 may be attached to a coaxial tube located within the lumen of the pusher 16 around the delivery element 42.

In operation, the extraction member can be deployed either prior to complete deployment of the flow restoration member 14 or after complete deployment of the flow restoration member 14.

Figure 25:
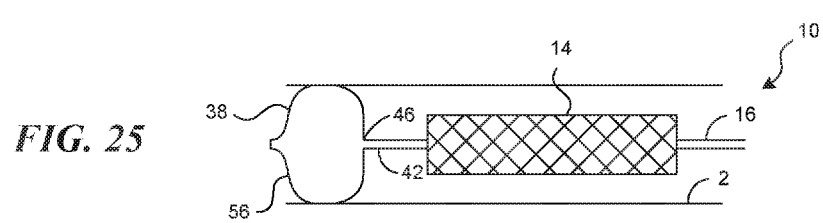
FIG. 25 is a partial cutaway view of a portion of an occlusion management system within a lumen of a patient according to one embodiment of the present invention.

In certain embodiments, as shown in FIG. 25, the extraction member 38 is a balloon 56 that is attached to a distal end 46 of a delivery element 42. The delivery element 42 has a lumen formed therethrough for inflation and deflation of the balloon 56. The balloon 56 having a diameter that is substantially equal to or greater than a diameter of the vessel 2.

Figure 26:
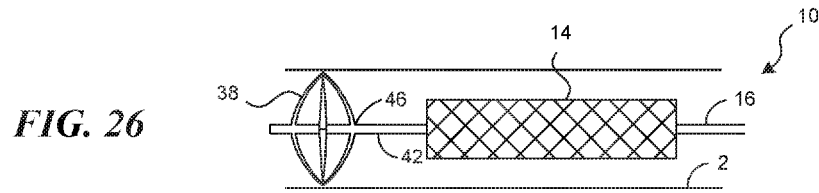
FIG. 26 is a partial cutaway view of a portion of an occlusion management system within a lumen of a patient according to one embodiment of the present invention.

In certain other embodiments, as shown in FIG. 26, the extraction member 38 is formed by a malecot-type formation of the distal end 46 of the delivery element 42. The malecot-type formation may be covered with a fabric, polymer, or braided covering. The malecot-type formation has a diameter that is substantially equal to or greater than a diameter of the vessel 2.

In certain other embodiments, as shown in FIG. 29 the extraction member 38 is formed of a braided structure having a disc-like form that is attached to a distal end 46 of a delivery element 42. The disc-like structure has a diameter that is substantially equal to or greater than a diameter of the vessel 2.

In one embodiment of the present invention, as shown in FIG. 7, the delivery element 42 is not employed in the system 10 and extraction member 38 is attached directly to the flow restoration member 14 by the tethers 40. More particularly, proximal ends of the tethers 40 are attached to the distal portion 34 of the flow restoration member 14 and distal ends of the tethers 40 are attached to the proximal periphery 48 of the extraction member 38.

In operation, after the catheter 12 is advanced through the occlusive material 4 until a distal end 24 of the catheter 12 passes entirely through the occlusive material 4, the catheter 12 is then retracted relative to the pusher 16. As the extraction member 38 is exposed from the retracting distal end 24 of the catheter 12, the extraction member 38 radially expands distally of the occlusive material 4. As the catheter 12 is further retracted, the flow restoration member 14 radially expands within the occlusive material 4.

After complete expansion of the flow restoration member 14, the pusher 16 is retracted relative to the catheter, thereby pulling the flow restoration member 14 through the occlusive material 4 and pulling the extraction member 38 into and around the occlusive material 4. The occlusive material 4 is thereby captured within the extraction member 38. Retraction of the pusher 16 is continued until the flow restoration member 14 and extraction member 38 with captured occlusive material 4 are pulled back into the lumen 22 of the catheter 12. The system 10 is then withdrawn from the patient.

The extraction member 38 may be formed at least in part by a braid of filaments or fabricated by methods known in the art of stent manufacturing including but not limited to conventional machining, laser cutting, electrical discharge machining (EDM) and photo-chemical etching.

Figure 10:
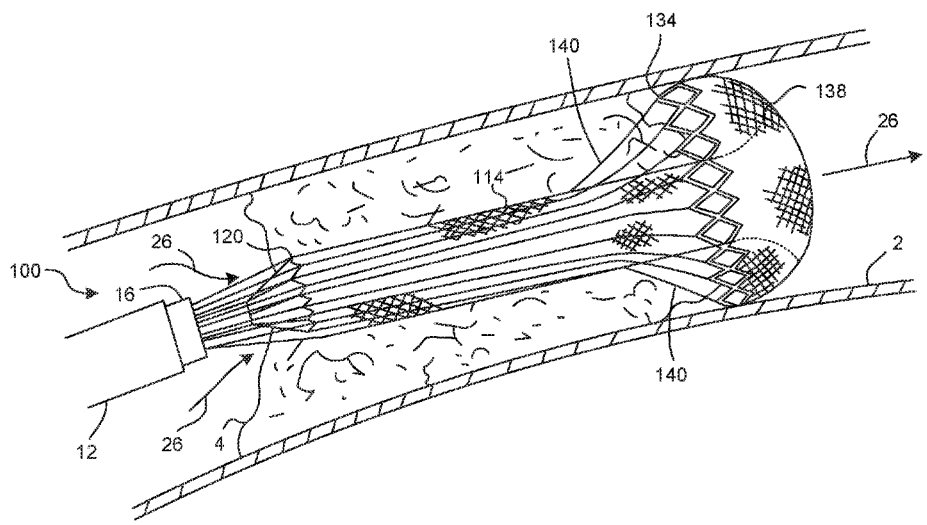
FIG. 10 is a partial cutaway view of a portion of an occlusion management system within a lumen of a patient according to one embodiment of the present invention.
Figure 11:
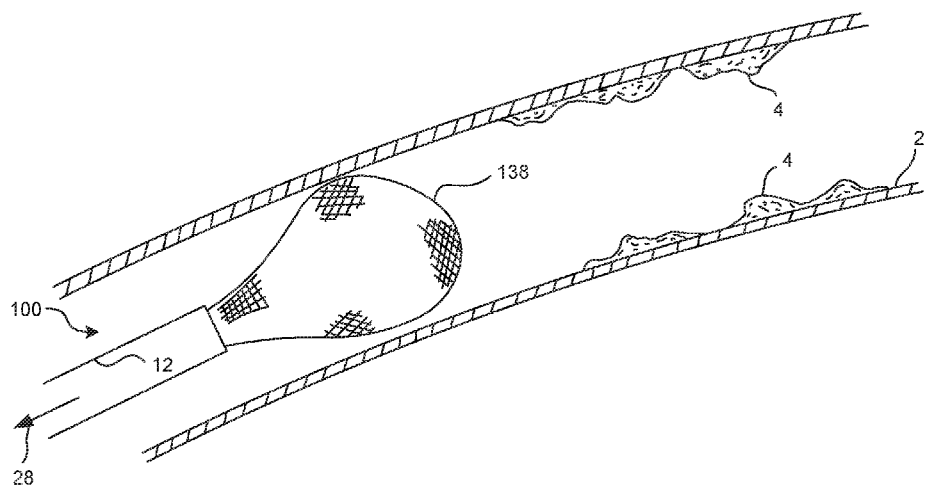
FIG. 11 is a partial cutaway view of a portion of an occlusion management system within a lumen of a patient according to one embodiment of the present invention.

In one embodiment of the present invention, as shown in FIGS. 8-11, the flow restoration member and the extraction member of the occlusion management system 100 are formed of a substantially continuous structure. For example, as shown in FIG. 10, a distal portion 134 of a flow restoration member 114 is biased to evert to a relaxed state that turns in a proximal direction back towards a proximal portion 120 of the flow restoration member 114, thereby forming an extraction member 138. One or more tethers 140 are eccentrically coupled or attached to the distal portion 134 of a flow restoration member 114. In certain embodiments, a radially expandable connector member 150 may hold ends of the filaments that may be present at the distal portion 134 of a flow restoration member 114.

Proximal ends of the tethers 140 may extend proximally within the lumen 22 of the catheter 12 and may be manipulated by a physician in order to facilitate the formation of the everted distal portion 134 and extraction member 138 of the flow restoration member 114. In certain embodiments, the tethers 140 do not extend to a proximal end of the system 100 but rather are connected to an elongate retraction member that in turn extends proximally for manipulation by a physician. As shown in FIG. 10, the tethers 140 may further function to cut through the occlusive material 4 as the extraction member 138 is formed or when the pusher 16, the flow restoration member 114, and the extraction member 138 are retracted relative to the catheter 12.

In certain embodiments, as shown in FIG. 27, the flow restoration member 114 having everted distal portion 134 need not necessarily employ the tethers 140.

Figure 21:
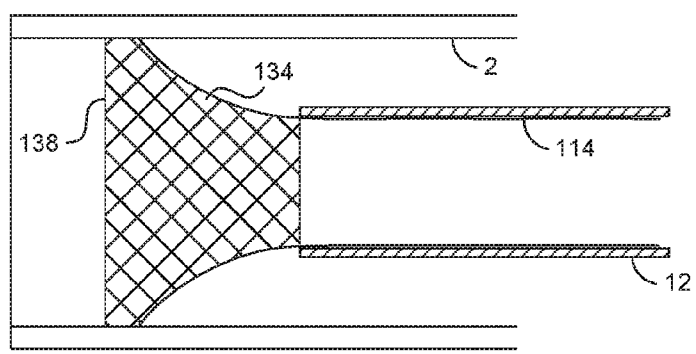
FIG. 21 is a partial cutaway view of a portion of an occlusion management system within a lumen of a patient according to one embodiment of the present invention.
Figure 22:
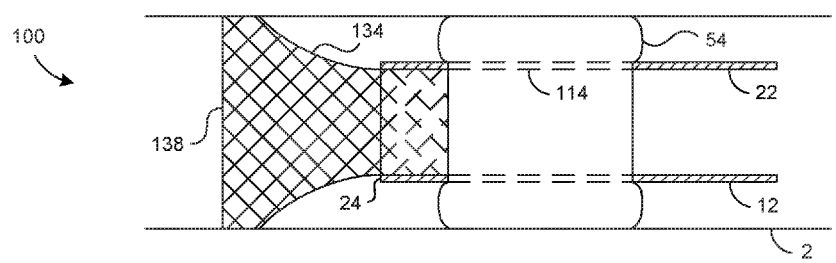
FIG. 22 is a partial cutaway view of a portion of an occlusion management system within a lumen of a patient according to one embodiment of the present invention.
Figure 23:
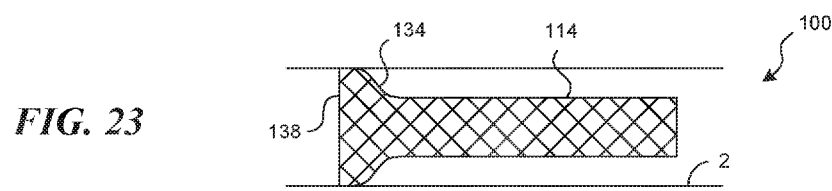
FIG. 23 is a partial cutaway view of a portion of an occlusion management system within a lumen of a patient according to one embodiment of the present invention.
Figure 24:
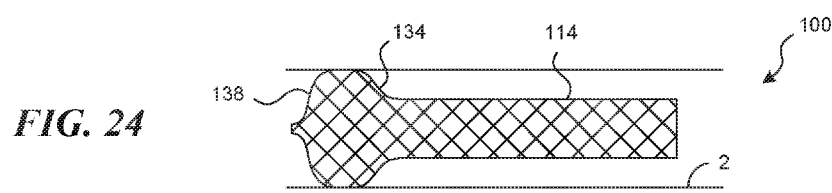
FIG. 24 is a partial cutaway view of a portion of an occlusion management system within a lumen of a patient according to one embodiment of the present invention.

In certain other embodiments, as shown in FIGS. 21-24, 28A, and 28B, the mesh or scaffold structure forming the flow restoration member 114 employs an enlarged diameter distal portion 134 that does not necessarily evert. For example, FIG. 21 shows a partially deployed and FIG. 23 shows completely deployed flow restoration member 114 having a flared or expanded distal portion 134. FIG. 24 shows the flow restoration member 114 having a bulbous, expanded distal portion 134 which may or may not employ a guide wire passage through a distal end.

In certain other embodiments, as shown in FIG. 28A and 28B, the extraction member 38 is a wireform attached to the delivery element, such as delivery element 42 described above, or alternatively attached directly to the flow restoration member 114 to form an expanded distal portion 134 of the flow restoration member 114. The wire form may also be covered with a braid. As shown in FIGS. 8-11, operation of the occlusion management system 100 is substantially the same as described above regarding the occlusion management system 10 employing the extraction member 38.

Figure 12:
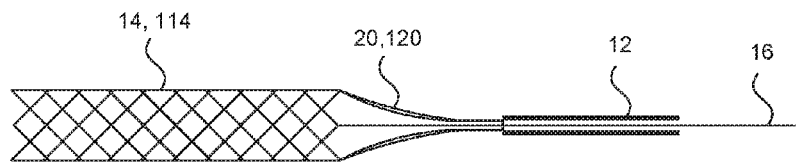
FIG. 12 is a partial cutaway elevation view of a portion of an occlusion management system according to one embodiment of the present invention.

In one embodiment of the present invention, as shown in FIG. 12, the pusher 16 may be formed of a wire, tube, or catheter.

Figure 13:
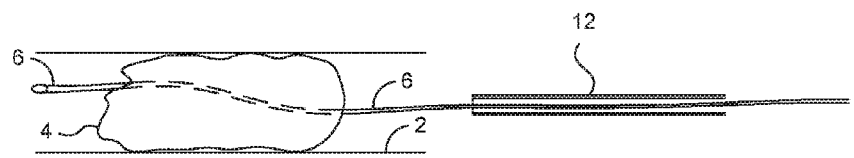
FIG. 13 is a partial cutaway view of a portion of an occlusion management system within a lumen of a patient according to one embodiment of the present invention.
Figure 14:
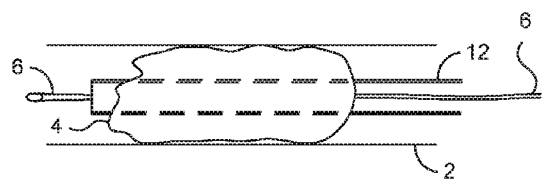
FIG. 14 is a partial cutaway view of a portion of an occlusion management system within a lumen of a patient according to one embodiment of the present invention.
Figure 15:
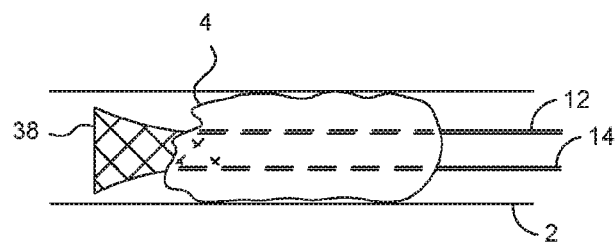
FIG. 15 is a partial cutaway view of a portion of an occlusion management system within a lumen of a patient according to one embodiment of the present invention.
Figure 16:
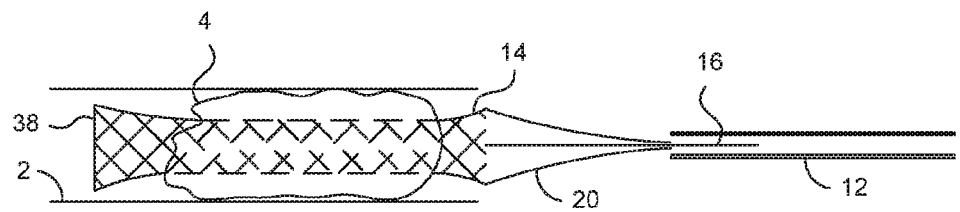
FIG. 16 is a partial cutaway view of a portion of an occlusion management system within a lumen of a patient according to one embodiment of the present invention.

In one embodiment of the present invention, as shown in FIGS. 13-19, a method for operation of system 10, 100 is shown. First, retrieval of occlusive matter 4 includes first advancing a guidewire 6 through a lumen 2 to the site of the occlusive material 4 and through the occlusive material 4. The catheter 12 is then advanced over the guidewire 6 to the site of the occlusive material 4 and through the occlusive material 4, as shown in FIGS. 13 and 14. The guidewire 6 is withdrawn from the patient. As shown in FIG. 15, the catheter 12 is then retracted relative to the pusher 16, thereby allowing the flow restoration member 14 to expand to a more relaxed state and engage the occlusive material 4.

Figure 17:
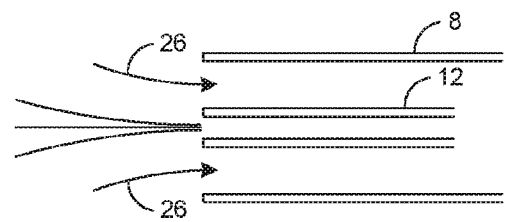
FIG. 17 is a partial cutaway view of a portion of an occlusion management system according to one embodiment of the present invention.
Figure 18:
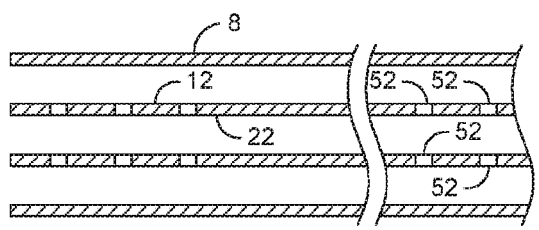
FIG. 18 is a partial cutaway view of a portion of an occlusion management system according to one embodiment of the present invention.

In certain embodiments, as shown in FIG. 17, the catheter 12 may be passed through a lumen of a sheath 8. The sheath 8 may function to provide suction, vacuum, or irrigation, in the direction of arrows 26, within the lumen 2 near the site of the occlusive material 4. Alternatively, as shown in FIG. 18, one or more holes 52 may be formed in the catheter 12 so that the suction, vacuum, or irrigation may originate from a proximal end of the catheter 12 and be simultaneously generated through the proximal portions of both the lumen 22 of the catheter 12 and the lumen of the sheath 8.

Figure 19:
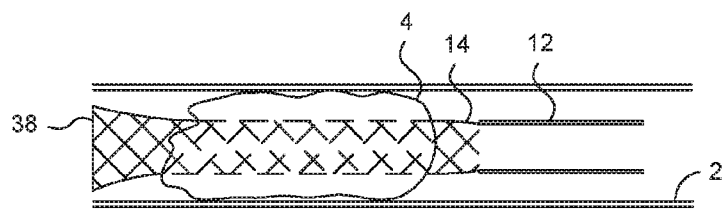
FIG. 19 is a partial cutaway view of a portion of an occlusion management system within a lumen of a patient according to one embodiment of the present invention.

With the assistance of such suction, vacuum, or irrigation, as shown in FIG. 19, it may be possible for the flow restoration member 14 to sufficiently engage the occlusive material 4 such that the occlusive material 4 is released from the lumen 2 and can be extracted in substantially its entirety from the lumen 2 of the patient.

Figure 20:
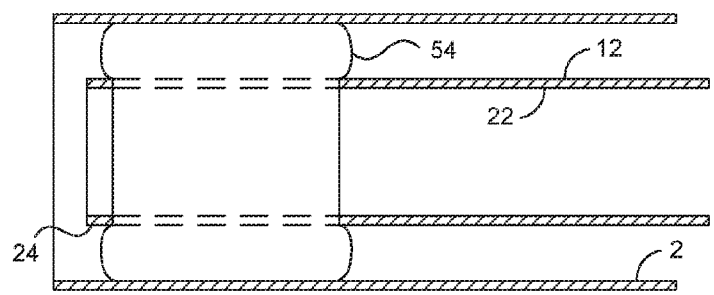
FIG. 20 is a partial cutaway view of a portion of an occlusion management system within a lumen of a patient according to one embodiment of the present invention.

In one embodiment of the present invention, as shown in FIG. 20, in order to further assist in the generation and efficacy of such suction, vacuum, or irrigation, an annular balloon 54 may be attached to an exterior of the catheter 12 near the distal end 24 of the catheter 12. The balloon 54 is sized so as to contact a circumference of an interior surface of the lumen 2. Accordingly, the balloon 54 provides a seal against the flow of fluid, such as blood, through the lumen 2 and enhances the efficacy of the suction, vacuum, or irrigation. FIG. 22 shows the flow restoration member 114 of FIG. 23 being deployed through a catheter 12 having an inflated balloon 54 near the distal end 24 of the catheter 12. In order to inflate and deflate the balloon 54, inflation lumens may be formed within the wall of the catheter 12 according to techniques known in the art.

In one embodiment of the present invention, as shown in FIGS. 30-35, an occlusion management system 200 employs a flow restoration member 214, such as that described above with respect to the flow restoration members 14 or 114 that is advanceable through a proximal capture member 260.

The proximal capture member 260 is radially expandable from compressed delivery state within a lumen 258 of a sheath 208, to a radially expanded, minimum energy state having a generally cylindrical or tubular shape. When in the expanded minimum energy state, the proximal capture member 260 may have a diameter that is larger or substantially equal to the diameter of the patient's lumen 2 in which the system 200 will be employed.

The proximal capture member 260 is attached to a capture member pusher 262 that is also inserted through the lumen 258 of the sheath 208. The proximal capture member 260 may be formed of a mesh or scaffold. The mesh or scaffold may be formed at least in part by a braid of filaments or fabricated by methods known in the art of stent manufacturing including but not limited to conventional machining, laser cutting, electrical discharge machining (EDM) and photo-chemical etching.

The flow restoration member 214 is attached to the pusher 16 and the flow restoration member 214 and the pusher 16 are positioned within the lumen 22 of the catheter 12. The catheter 12 is, in turn, positioned within a lumen of the proximal capture member 260. A diameter of the proximal capture member 260 may be approximately equal to or greater than a diameter of the lumen 2.

In operation, the capture member pusher 262 and attached proximal capture member 260 are inserted into the lumen 258 of the sheath 208. A guidewire may be advance through the occlusion material 4, such as a thrombus or embolus. The sheath 208 is then advanced over the guidewire to a position proximal of the occlusion material 4. The guidewire may but need not necessarily be retracted at this time.

Figure 30:
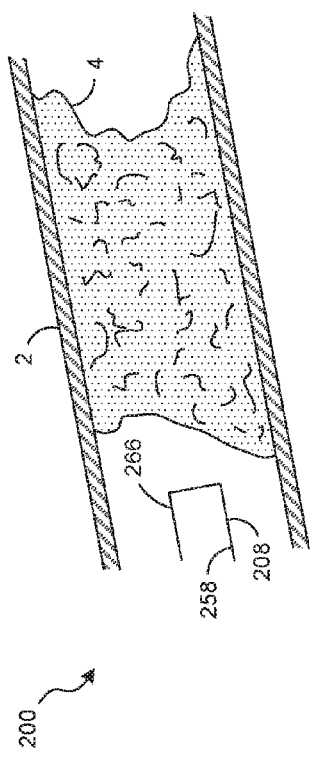
FIG. 30 is a partial cutaway view of a portion of an occlusion management system within a lumen of a patient according to one embodiment of the present invention.
Figure 31:
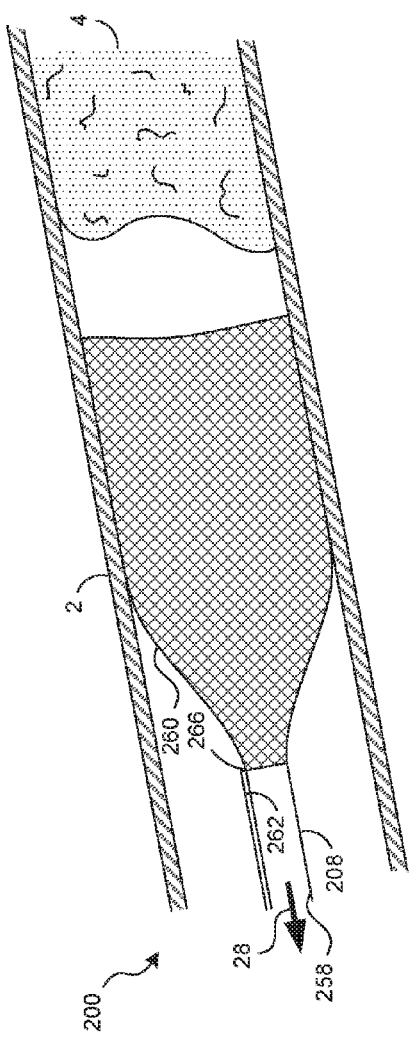
FIG. 31 is a partial cutaway view of a portion of an occlusion management system within a lumen of a patient according to one embodiment of the present invention.

As shown in FIGS. 30 and 31, the sheath 208 is retracted, in the direction of arrow 28, proximally relative to the capture member pusher 262, thereby exposing the proximal capture member 260 at a distal end 266 of the sheath 208 and allowing the proximal capture member 260 to radially expand from its collapsed state within the lumen 258 of the sheath 208.

Figure 32:
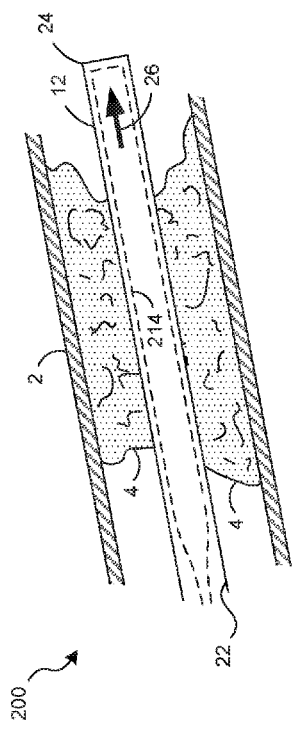
FIG. 32 is a partial cutaway view of a portion of an occlusion management system within a lumen of a patient according to one embodiment of the present invention.
Figure 33:
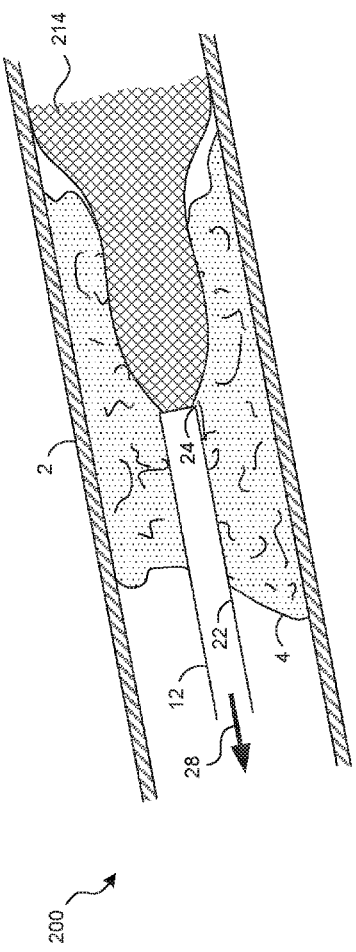
FIG. 33 is a partial cutaway view of a portion of an occlusion management system within a lumen of a patient according to one embodiment of the present invention.
Figure 34:
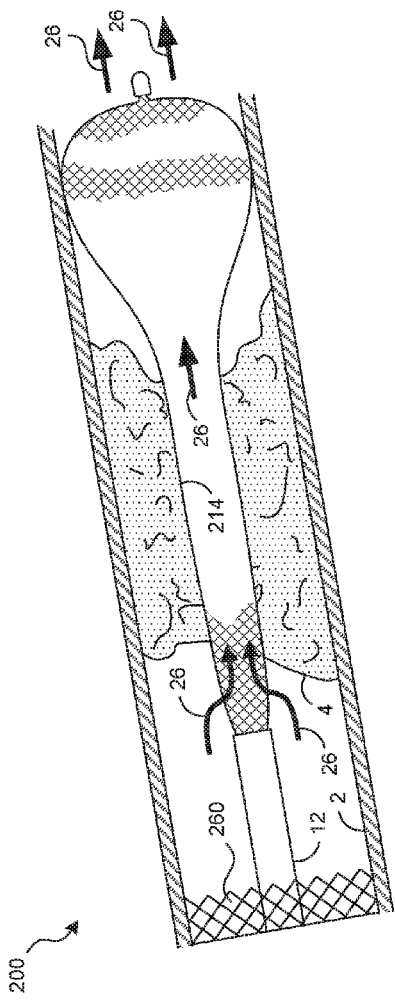
FIG. 34 is a partial cutaway view of a portion of an occlusion management system within a lumen of a patient according to one embodiment of the present invention.

The pusher 16 and attached flow restoration member 214 are then inserted into the lumen 22 of the catheter 12. As shown in FIG. 32, the catheter 12 is then advanced through the lumen 258 of the sheath 208 and the lumen of the proximal capture member 260 until a distal end 24 of the catheter 12 is positioned distally of the occlusive material 4. As shown in FIGS. 33 and 34, the catheter 12 is then retracted, in the direction of arrow 28, proximally relative to the flow restoration member 214, thereby exposing the flow restoration member 214 and allowing the flow restoration member 214 to radially expand from its collapsed state within the lumen 22 of the catheter 12.

Figure 35:
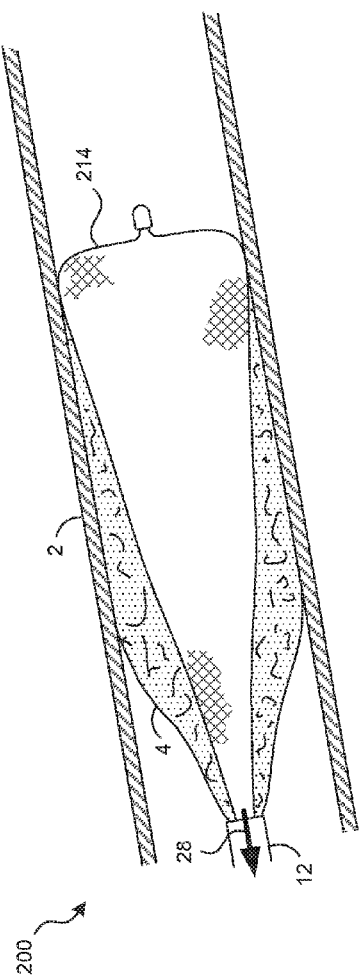
FIG. 35 is a partial cutaway view of a portion of an occlusion management system within a lumen of a patient according to one embodiment of the present invention.

As shown in FIG. 35, after complete expansion of the flow restoration member 214, the pusher 16 is retracted relative to the catheter 12, thereby pulling the flow restoration member 214 through the occlusive material 4 and pulling an extraction member, if present, into and around the occlusive material 4. The occlusive material 4 is thereby captured within the flow restoration member 214 and extraction member, if present. Retraction of the pusher 16 is continued until the flow restoration member 214 and extraction member, if present, with captured occlusive material 4 are pulled at least partially back into the lumen 22 of the catheter 12. The catheter 12 and the flow restoration member 214 and extraction member, if present, with captured occlusive material 4 are then pulled back into the lumen 264 of the proximal capture member 260. The proximal capture member 260 is then pulled back into the lumen 258 of the sheath 208. The system 200 is then withdrawn from the patient.

The order of deployment of the proximal capture member 260 and flow restoration member 214 as described above may be reversed as seen fit by the physician. Furthermore, therapeutic agent(s) such as thrombolytics or anticoagulants may be infused through the lumen 258 of the sheath 208 or lumen 22 of catheter 12 during the course of the procedure.

Figure 36:
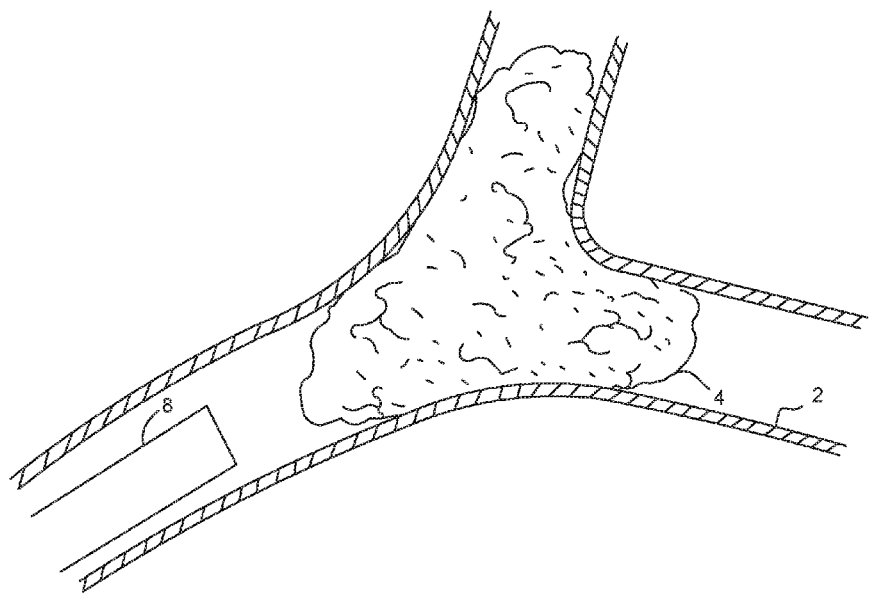
FIG. 36 is a partial cutaway view of a portion of an occlusion management system within a lumen of a patient according to one embodiment of the present invention.
Figure 37:
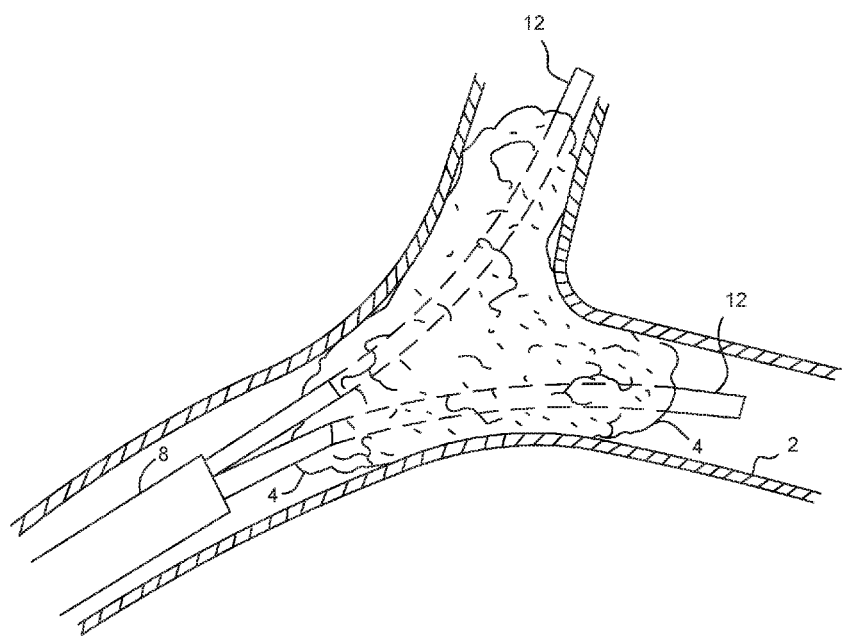
FIG. 37 is a partial cutaway view of a portion of an occlusion management system within a lumen of a patient according to one embodiment of the present invention.

In one embodiment of the present invention, the occlusion management systems 10, 100, 200 is configured for removal of at least a portion of the occlusive material 4, such as an embolus or thrombus, that is located at a bifurcation, trifurcation or multi-lumen plexus of the lumen 2, such as a blood vessel. By way of example, as shown in FIGS. 36 and 37, a sheath 8, through which multiple catheters 12 are inserted, is advanced through the lumen 2 to the bifurcation at which occlusive material 4 is present. The catheters 12 are independently advanced distally from the sheath 8 through the occlusive material 4 within the different lumens 2 of the bifurcation. Flow restoration and extraction of the occlusive material 4 is conducted as described above.

In certain embodiments of the present invention, the flow restoration member 14, 114, 214, extraction member 38, 138, and the proximal capture member 260 may comprise a braided mesh of filaments or wires 70. The braids for the mesh components may have a generally constant braid angle over an entire length of the member or may be varied to provide different zones of pore size and radial stiffness.

The braided mesh may be formed over a mandrel as is known in the art of tubular braid manufacturing. A braid angle a (alpha), shown in FIG. 38, may be controlled by various means known in the art of filament braiding. In certain embodiments, the braid angle a is, for example, between about 45 degrees and about 60 degrees. The tubular braided mesh may be further shaped using a heat setting process. As known in the art of heat setting nitinol wires, a fixture, mandrel or mold may be used to hold the braided tubular structure in its desired configuration then subjected to an appropriate heat treatment such that the resilient filaments of the braided tubular member assume or are otherwise shape-set to the outer contour of the mandrel or mold.

In certain embodiments, the filamentary elements of the mesh member may be held by a fixture configured to hold the member in a desired shape and heated to about 475-525 degrees Celsius for about 5 to 30 minutes to shape-set the structure. In certain embodiments, the braid may be a tubular braid of fine metal wires 70 such as Nitinol, platinum, cobalt-chrome alloys, 35N LT, Elgiloy, stainless steel, tungsten or titanium.

In certain embodiments, the member can be formed at least in part from a cylindrical braid of elastic filaments. Thus, the braid may be radially constrained without plastic deformation and will self-expand on release of the radial constraint to an unrestrained diameter or diameter at its lowest energy state. Such a braid of elastic filaments is herein referred to as a "self-expanding braid."

In certain embodiments, the thickness of the braid filaments is less that about 0.5 millimeters. In certain embodiments, the braid may be fabricated from wires 70 with diameters ranging from about 0.015 millimeters to about 0.40 millimeters. In certain embodiments, the braid may be fabricated from wires with diameters ranging from about 0.02 millimeters to about 0.15 millimeters.

In certain embodiments, the member has a high braid angle zone where the braid angle a is greater than about 60 degrees. More particularly, the higher braid angle portion or zone may have a braid angle a that is between 60 and 80 degrees. The high braid angle portion may have higher radial stiffness that may provide, for example, improved extraction of occlusive material 4. Furthermore, as the member is retracted the portion of the member with a high braid angle elongates to a greater amount relative to the remainder of the member, thereby providing a longer surface for retraction through the occlusive material.

Figure 38:
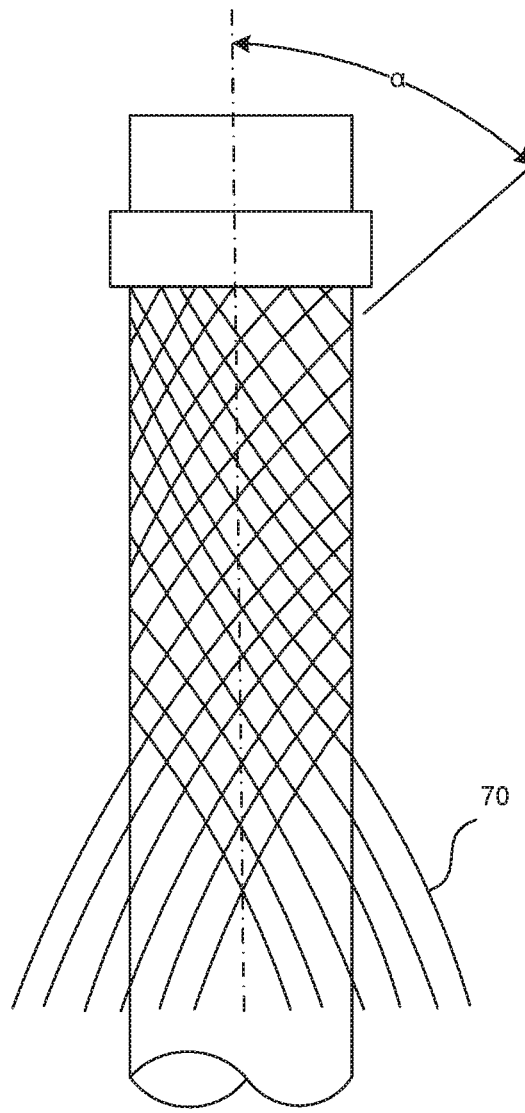
FIG. 38 is an elevation view of a portion of an occlusion management system according to one embodiment of the present invention.
Figure 39:
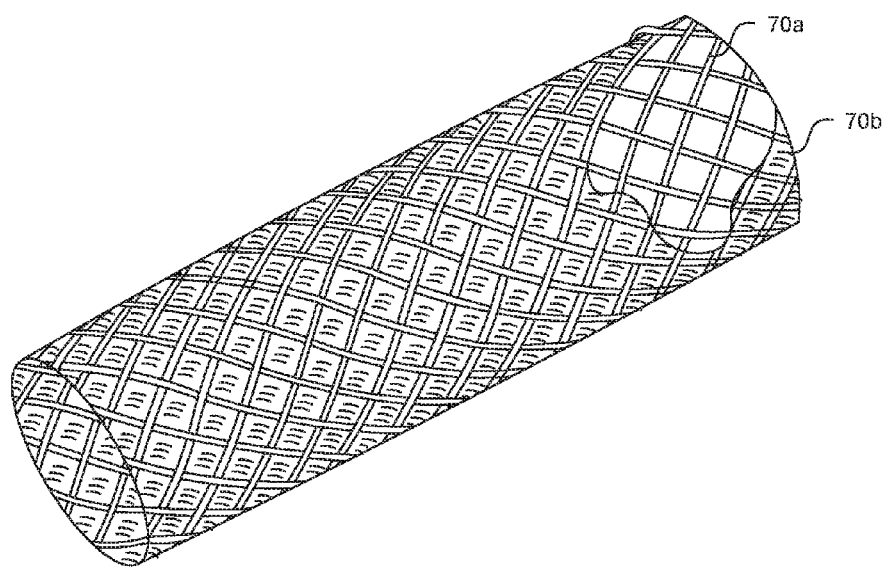
FIG. 39 is a perspective view of a portion of an occlusion management system according to one embodiment of the present invention.

In certain embodiments, the system may comprise a braided member where the braid is formed from a mixture of more than one diameter wire 70, as shown in FIG. 38. A braid showing two wire diameters, wire 70a and wires 70b having a smaller diameter than the diameter of the wires 70a, is shown in FIG. 39.

A braided member may also comprise a plurality of layers. In certain embodiments, the system may comprise a braided member where the braid configuration changes over the length of the member forming a tubular structure with two or more zones of different braid. The parameters that may be changed to manipulate the braid include but are not limited to braid angle a, combinations of different diameters of wire 70 (e.g. a combination of small and large diameters) and wire loading (e.g. alternating wire size in a 1 by 1 or 2 by 2 pattern). Changing the braid parameters allows for zones of different mechanical properties (e.g. radial stiffness and compliance) along one continuous braid. In certain embodiments, the member may have one zone with a braid angle a between about 35 degrees and 55 degrees and another zone with a braid angle a between about 50 degrees and 70 degrees. In certain embodiments, the member may have one zone with a radial stiffness that is at least about 25% greater than the radial stiffness of a second zone.

In one embodiment of the present invention, as shown in FIGS. 40A-40C, the flow restoration member may be formed by machining or laser cutting a stent-like pattern either directly in a tube or in a flat sheet that is subsequently formed into a tube. The sheet may be rolled or otherwise formed into a generally tubular configuration and then welded, soldered or joined in order to fix the tubular shape. FIG. 40A shows an exemplary flat pattern. FIG. 40B shows the tube form of the stent-like pattern and FIG. 40C shows the stent-like tube attached to the distal end of a pusher or delivery element. In certain other embodiments, as shown in FIG. 27, the extraction member 138 is a braided structure extension of flow restoration member 114 that has been everted and curled back on itself forming an expanded distal portion. In any of the above described embodiments, the system 10, 10, 200 may include additional devices or components to facilitate thrombus maceration or disruption including but not limited to mechanical maceration members (auger, drill bit, screw, impellor, burr, pick, etc.), vibration members, ultrasonic energy, radiofrequency energy, microwave energy, thermal energy, cavitiation, flow jets or perfusion apparatus. For example, in certain embodiments, the system 10, 100, 200 may comprise a boring member to facilitate penetration of the occlusive material 4. In certain embodiments, the system 10, 100, 200 may comprise an auger device to facilitate retraction of the occlusive material 4, such as thrombus along a central path coaxial with the flow restoration member 14, 114, 214.

In any of the above described embodiments, the system 10, 100, 200 may include a drug or bioactive agent to enhance the thrombus extraction performance and/or reduce the propensity to produce clotting. In certain embodiments, the system 10, 100, 200 and more particularly the flow restoration member 14, 114, 214, extraction member 38, 138, and the proximal capture member 260 may employ textures, surface features, coatings, or the like to enhance the engagement and/or attachment of the occlusive material 4, such as thrombus. In certain embodiments, the device may include an antiplatelet agent, a lytic agent or an anticoagulant.

In any of the above described embodiments, a delivery system may be provided or integrated into the catheter 10 and/or sheath 8, 208. The delivery system may include an introducer sheath for access into the appropriate vein such as the subclavian vein, jugular vein, femoral vein or radial vein. In certain embodiments, the catheter 10 and/or sheath 8, 208 may be placed through the introducer sheath to pass through the access vein such as the right subclavian vein or jugular vein into the superior vena cava through the right atrium through the tricuspid valve, through the right ventricle, through the pulmonic valve, to thrombus or occlusive embolus situated in the pulmonary artery or branches of the pulmonary artery. In some embodiments, the catheter 10 and/or sheath 208 may be placed through the introducer sheath to pass through the access vein such as the femoral vein into the inferior vena cava through the right atrium through the tricuspid valve, through the right ventricle, through the pulmonic valve, to thrombus or occlusive embolus situated in the pulmonary artery or branches of the pulmonary artery.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method for removal of thrombus from a peripheral blood vessel in a body of a patient, the method comprising:
 providing a thrombus extraction device comprising a scaffold member formed of a tubular fenestrated structure with an open proximal end having a perimeter and an open distal end, a capture member formed of a mesh structure which is fixedly attached to the proximal end of the scaffold member, and a pusher connected to a proximal end of the mesh structure;
 advancing a catheter constraining the thrombus extraction device through the thrombus located in the peripheral vasculature of a patient's body;
 deploying the thrombus extraction device, wherein the deployed thrombus extraction device comprises an everted distal portion of the capture member, wherein deploying the thrombus extraction device comprises expanding the scaffold member and expanding the everted distal portion of the capture member, and wherein deploying the thrombus extraction device comprises advancing a portion of the capture member through the scaffold member to create the everted distal portion of the capture member;
 retracting the thrombus extraction device to capture thrombus within the everted distal portion of the capture member; and withdrawing the thrombus extraction device from the body of the patient.

2. The method of claim 1, wherein the distal end of the capture member is biased to evert in a relaxed state.

3. The method of claim 1, wherein retracting the thrombus extraction device into the catheter constrains the thrombus extraction device and the captured thrombus within the catheter.

4. The method of claim 1, further comprising inserting the catheter constraining the thrombus extraction device into a peripheral vein in a leg of the patient.

5. The method of claim 4, wherein the peripheral vein comprises a deep vein.

6. The method of claim 5, wherein the peripheral vein comprises the femoral vein.

7. The method of claim 1, wherein retracting the thrombus extraction device to capture thrombus within an everted distal portion of the capture member comprises capturing at least a portion of the thrombus between the everted distal portion of the capture member and a non-everted portion of the capture member.

8. The method of claim 1, wherein the scaffold member and the capture member form a continuous structure.

9. The method of claim 1, wherein deploying the thrombus extraction device further comprises everting the scaffold member.

10. The method of claim 1, wherein deploying the thrombus extraction device comprises relatively retracting an elongate retraction member coupled to the distal end of the scaffold member with respect to the pusher.

11. The method of claim 1, wherein deploying the thrombus extraction device comprises manipulating at least one tether coupled to the distal end of the scaffold member with respect to the pusher.

12. The method of claim 1, wherein the distal portion of the capture member is everted in the patient's body.

13. The method of claim 1, wherein the thrombus extraction device is deployed distal of the thrombus.

14. A method for removal of thrombus from a peripheral blood vessel in a body of a patient, the method comprising:
  providing a thrombus extraction device comprising a scaffold member formed of a tubular fenestrated structure with an open proximal end having a perimeter and an open distal end, a tapered capture member formed of a mesh structure which is attached at a proximal end of the tapered capture member to the distal end of the scaffold member so as to form a continuous structure, and a retraction member connected to a proximal end of the scaffold member;
  advancing a catheter constraining the thrombus extraction device through the thrombus located in the peripheral vasculature of a patient's body;
  deploying the thrombus extraction device, wherein the deploying the thrombus extraction device comprises expanding the scaffold member, and wherein the deploying the thrombus extraction device comprises expanding the tapered capture member subsequent to expanding the scaffold member;
  retracting the thrombus extraction device through the thrombus;
  separating the thrombus from the peripheral blood vessel with the scaffold member; and
  capturing the thrombus within the tapered capture member.

15. The method of claim 14, further comprising withdrawing the thrombus extraction device from the body of the patient.

16. The method of claim 14, wherein the deploying the thrombus extraction device comprises retracting the catheter relative to the retraction member until the scaffold member is exposed.

17. The method of claim 14, wherein retracting the thrombus extraction device through the thrombus comprises retracting the retraction member relative to the catheter through a lumen of the catheter.

18. The method of claim 14, wherein the thrombus extraction device further comprises a pusher connected to a second end of the tapered capture member.

19. The method of claim 18, further comprising controlling a length of the tapered capture member beyond the scaffold member via a relative position of the pusher with respect to the retraction member.

20. A method for removal of thrombus from a peripheral blood vessel in a body of a patient, the method comprising:
  providing a thrombus extraction device comprising a scaffold member formed of a tubular fenestrated structure with an open proximal end having a perimeter and an open distal end, and a capture member formed of a mesh structure which is attached to the proximal end of the scaffold member at a distal end of the capture member so as to form a continuous structure;
  advancing a catheter constraining the thrombus extraction device through the thrombus located in the peripheral vasculature of a patient's body;
  deploying the thrombus extraction device, wherein the deployed thrombus extraction device comprises an everted distal portion of the capture member, wherein deploying the thrombus extraction device comprises expanding the scaffold member and expanding the everted distal portion of the capture member, and wherein deploying the thrombus extraction device comprises advancing a portion of the capture member through the scaffold member to create the everted distal portion of the capture member;
  retracting the thrombus extraction device to capture thrombus within an everted distal portion of the capture member; and
  withdrawing the thrombus extraction device from the body of the patient.

21. The method of claim 20, further comprising inserting the catheter constraining the thrombus extraction device into a peripheral vein in a leg of the patient.

22. The method of claim 21, wherein the peripheral vein comprises a deep vein, and wherein the deep vein comprises the femoral vein.

23. The method of claim 20, wherein retracting the thrombus extraction device to capture thrombus within an everted distal portion of the capture member comprises capturing at least a portion of the thrombus between the everted distal portion of the capture member and a non-everted portion of the capture member.

24. The method of claim 20, wherein deploying the thrombus extraction device comprises relatively retracting an elongate retraction member coupled to the distal end of the scaffold member.

25. The method of claim 20, wherein the thrombus extraction device is deployed distal of the thrombus.

* * * * *